(12) United States Patent
Malackowski

(10) Patent No.: US 7,753,880 B2
(45) Date of Patent: Jul. 13, 2010

(54) METHOD OF OPERATING A SURGICAL IRRIGATION PUMP CAPABLE OF PERFORMING A PRIMING OPERATION

(75) Inventor: Don Malackowski, Schoolcraft, MI (US)

(73) Assignee: Stryker Corporation, Kalamazoo, MI (US)

( * ) Notice: Subject to any disclaimer, the term of this patent is extended or adjusted under 35 U.S.C. 154(b) by 1074 days.

(21) Appl. No.: 10/952,410

(22) Filed: Sep. 28, 2004

(65) Prior Publication Data
US 2006/0073048 A1 Apr. 6, 2006

(51) Int. Cl.
*A61M 37/00* (2006.01)
*A61B 17/32* (2006.01)

(52) U.S. Cl. ............... 604/131; 604/65; 604/66; 604/67; 604/118; 606/170; 417/477.2; 318/432; 318/799; 318/806

(58) Field of Classification Search ............... 604/19, 604/131, 118, 35, 22, 65, 67; 417/474, 477.2; 606/170, 167, 180; 318/432, 799, 806
See application file for complete search history.

(56) References Cited

U.S. PATENT DOCUMENTS

| | | | |
|---|---|---|---|
| 5,400,267 A | 3/1995 | Denen et al. | |
| 5,460,490 A | 10/1995 | Carr et al. | 417/44.2 |
| 5,628,731 A | 5/1997 | Dodge et al. | 606/153 |
| 5,810,770 A * | 9/1998 | Chin et al. | 604/65 |
| 5,885,245 A * | 3/1999 | Lynch et al. | 604/67 |
| 6,007,556 A | 12/1999 | Kablik | 606/180 |
| 6,017,354 A | 1/2000 | Culp | 606/170 |
| 6,269,340 B1 * | 7/2001 | Ford et al. | 705/3 |
| 6,285,285 B1 | 9/2001 | Mongrenier | |
| 2001/0020148 A1 | 9/2001 | Sasse et al. | |
| 2003/0093103 A1 | 5/2003 | Malackwski et al. | 606/170 |

FOREIGN PATENT DOCUMENTS

WO  WO 03/013372  2/2003

OTHER PUBLICATIONS

EPO, International Search Report and ISA Written Opinion for PCT App. No. PCT/PCTUS2005/033212, Feb. 2006.
Stryker TPS Console, List of Supplemental Commands, Jan. 2002 (1 page).

* cited by examiner

*Primary Examiner*—Nicholas D Lucchesi
*Assistant Examiner*—Quynh-Nhu H Vu

(57) ABSTRACT

A tool system for operating an irrigation pump. The pump includes a fixed pump head driven by a pump motor and a removable tube set. A readable memory such as a RFID is integral with the tube set. The tube set memory contains data describing the physical characteristics of the tube set. A control console reads the data in the tube set memory. Based on these data, the control console then regulates the operation of the pump motor so that fluid, when required, is delivered at those flow rates. These data are also used by the control console to regulate priming of the pump so that when the system is initially set up a head of irrigation fluid can be pumped close to the end of the handpiece from which the fluid is to be discharged.

20 Claims, 14 Drawing Sheets

| MIN. FLOW RATE | 74 |
|---|---|
| DEFAULT FLOW RATE | 76 |
| MAX FLOW RATE | 78 |

| FLUID TYPE | 302 |
|---|---|
| FLUID VOLUME | 304 |
| DATE OF MANUFACTURE | 306 |
| LOT NUMBER | 307 |

| | 81 |
|---|---|
| FAMILY CODE | 82 |
| DEVICE CODE | 83 |
| LENGTH | 84 |
| NOVRAM FORMAT REV | 86 |
| PART NO. | 88 |
| PART NAME | 90 |
| LOT IDENTIFICATION | 92 |
| MNFCTR IDENTIFICATION | 94 |
| DATA REV. | 96 |
| MIN. CNSL MJR HRDWR REV. | 100 |
| MIN. CNSL MJR SFTWR REV. | 102 |
| MIN CNSL MINR SFTWR REV. | 104 |
| TUBE IN LENGTH | 106 |
| TUBE OUT LENGTH | 108 |
| TUBE IN DIAMETER | 110 |
| TUBE OUT DIAMETER | 112 |
| FLOW PER RVLTN | 114 |

FIG. 5A

METHOD OF OPERATING A SURGICAL IRRIGATION PUMP CAPABLE OF PERFORMING A PRIMING OPERATION

FIELD OF THE INVENTION

This invention relates generally to a powered surgical tool system with a pump. More particularly, this invention relates to a powered surgical tool system wherein the operation of the pump is integrated with the operation of the surgical handpiece with which the pump is used.

BACKGROUND OF THE INVENTION

In modern surgery, one or more surgical sub-procedures are performed with powered surgical handpieces. A handpiece may include a motor that drives a cutting accessory such as a drill bit, saw blade or a bur. Alternatively, the handpiece may be an electrocautery device, or a tissue ablation tool that removes and/or shapes the tissue with RF energy, ultrasonic energy or light energy. The electrical energy used to actuate these handpieces often comes from a control console to which the handpiece is connected.

During the performance of many surgical procedures, it is often desirable to apply an irrigation fluid to the site at which the procedure is being performed. This fluid clears away debris that form during the procedure. Depending on the procedure and the preference of the surgeon, irrigation occurs simultaneously with the actuation of the tool performing the procedure and/or sequentially with the actuation of the handpiece. Often the irrigation fluid is introduced to the surgical site by an irrigation line that is temporarily or permanently attached to the handpiece. The distal end of this irrigation line is directed to the location to which the distal end of the handpiece, or any accessory attached to the handpiece, is applied to the patient in order to perform the desired surgical procedure. One assembly for removably attaching the distal end section of an irrigation line to a handpiece is disclosed in the Applicant's Assignee's U.S. Pat. No. 6,017,354, INTEGRATED SYSTEM FOR POWERED SURGICAL TOOLS, issued Jan. 25, 2000 the contents of which is explicitly incorporated herein by reference.

Irrigation fluid is supplied to the irrigation line through a pump. One popular form of pump used to supply this fluid is a peristaltic pump. Generally, a peristaltic pump includes a tube into which irrigating fluid is gravity flowed. An arcuate section of the tube rests against a concave surface. A set of rollers attached to a rotor press the tube against the curved surface. The action of the rollers pushing against the tube forces the fluid in the tube downstream so it is discharged at the surgical site. Often the tube is at least partially contained in a cassette. A portion of the tube extends outside of the cassette. The wall of the cassette adjacent where the tube is exposed forms the surface against which the tube bears. Each time a new surgical procedure is performed a tube set, consisting of the tube and cassette, is mounted to the pump. This provides efficient means for quickly mounting new, sterile, tubes to the pump. The Applicant's Assignee's U.S. Pat. No. 6,007,556, SURGICAL IRRIGATION PUMP AND TOOL SYSTEM, issued Dec. 28, 1999, and explicitly incorporated herein by reference, discloses one such pump assembly.

There has been increase in the number of surgical handpieces that are available to surgeons. For example, specialized powered handpieces are available to perform surgical procedures on the spine, other handpieces are available to perform sinus surgery while some are designed specifically for orthopedic repair or joint replacement procedures. Similarly, different tube sets are now available for use with the same basic pump consoles. For instance, tube sets primarily designed to provide large volumes of fluid are available for use to perform surgical procedures on large joints. Other tube sets are designed for use in small joint surgery. These tube sets are designed to provide irrigation fluid in smaller volumes than those designed for use during large joint procedures.

The availability of these different surgical tools and pump tube sets can potentially lead to confusion during a surgical procedure. For example, for any number of reasons, a large joint tube set may be attached to a pump when the pump is set for use in a procedure in which large amounts of irrigating fluid are neither required nor desirable. Similarly, a small joint tube set may be attached to a pump when the procedure to be performed is one in which most likely it is desirable to provide large volumes of irrigation fluid at relatively high flow rates. Taking the time to double check to ensure that the proper tube set is attached to a pump and/or having to quickly change the tube set if the oversight is not discovered, can increase the time it takes to perform a surgical procedure. This runs contrary to one of the goals of modern surgery which is to perform the surgical procedure as quickly as possible.

The Applicant's Assignee's U.S. Pat. No. 5,810,770, FLUID MANAGEMENT PUMP SYSTEM FOR SURGICAL PROCEDURES, issued Sep. 22, 1998, discloses a pump assembly wherein a tube set cassette is provided with a ROM. The ROM contains basic data identifying the type of tube set. Even providing this type of data cannot guarantee that the proper type of tube set will be installed in a pump for a given surgical procedure.

Still another problem with currently available pumps concerns their priming. Specifically, when a tube set is initially attached to a pump, irrigation fluid often does not flow through the tube set. If the pump is not primed, when the pump is initially actuated, there is a delay until the fluid is forced through the tube set and discharged. Presently, the only means by which this delay can be eliminated is to prime the pump by having operating room personnel turn the pump on for a short period of time to bring the fluid head close to the discharge outlet. Requiring surgical personnel to perform this task takes time and, in some situations, may take more time then simply waiting for the fluid to be discharged from an unprimed tube set. Moreover, it may be difficult for surgical personnel to accurately prime the tube set by turning the pump on and off. If the pump is turned on for too short a time, the tube set may be insufficiently primed. Alternatively, if the pump is turned on for too long a time period, irrigation fluid may be discharged from tube set. This discharge just needlessly adds to the presence of undesirable liquid-state waste material in the operating room.

SUMMARY OF THE INVENTION

This invention relates to a new and useful system for providing irrigation fluid to a site at which a surgical handpiece is applied. The surgical tool system of this invention includes a control console to which different surgical handpieces are removably attached. The control console is capable of supplying power to these handpieces. The control console also includes a pump head. The console is further designed so a tube set cassette can be removably coupled to the pump head. The handpieces associated with the system of this data have memories that describe their operating characteristics. These characteristics include the characteristics of the irrigation fluid flow that should be supplied when these handpieces are used. Integral with the tube set cassettes are additional memories. These memories describe the characteristics of the tube sets. A control processor integral with the control console reads the data in the handpiece memories and the tube set cassette memories.

Based on the data in the handpiece and tube set cassette memories, the control console processor determines whether or not the tube set will be able to supply the appropriate flow irrigating fluid to the surgical site. Based on these data, the control console processor is also capable of establishing the preferred flow rates for the fluid out of the pump.

Still another feature of this invention is that the control console processor, based on the read data, is able to prime the pump. That is, the control console actuates the pump for a fixed amount of time to cause the head of the fluid in the tube set to be forced relatively close to the distal end discharge opening.

BRIEF DESCRIPTION OF THE DRAWINGS

The invention is pointed out with particularity in the claims. The above and further features of the invention may be better understood by reference to the following description taken in conjunction with the accompanying drawings in which:

FIGS. 5A and 5B collective form a diagram depicting the different types of data stored in the tube set RFID chip.

DETAILED DESCRIPTION

Figure 1:
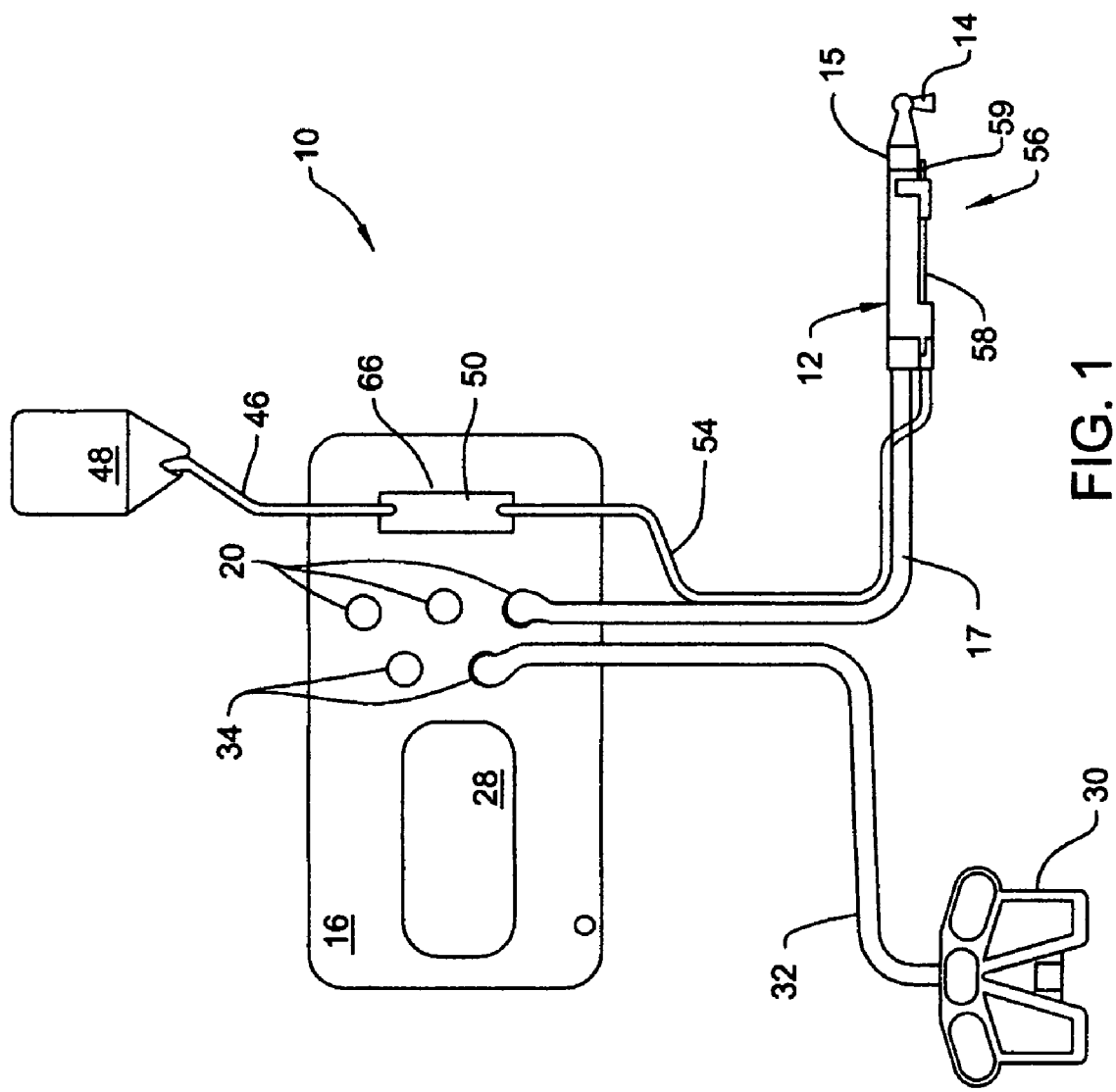
FIG. 1 depicts the basic components of the tool system of this invention.
Figure 2:
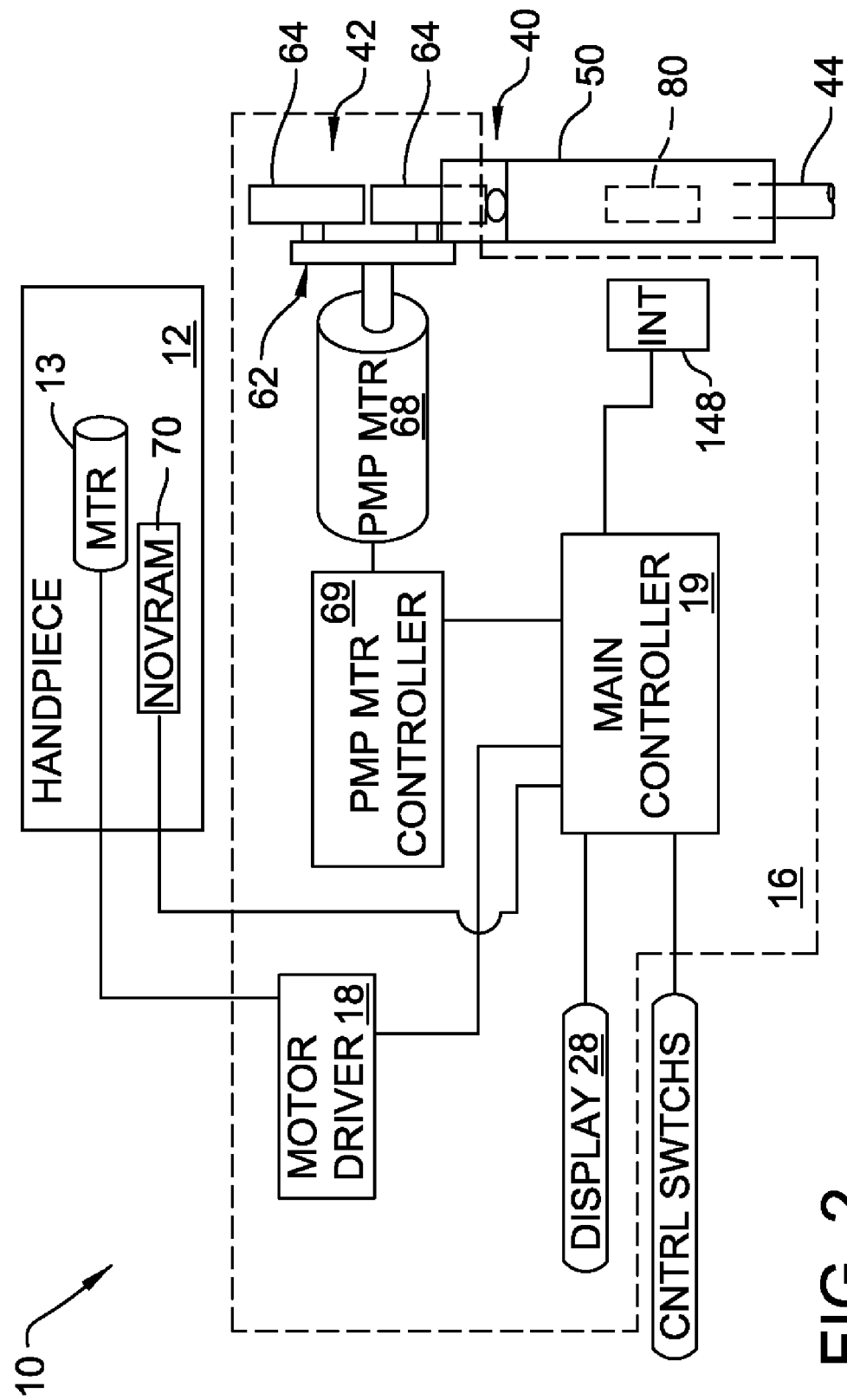
FIG. 2 is a block diagram of the internal components of the control console including the fixed, non-disposable, components of the pump.

FIGS. 1 and 2 illustrate the basic features of a surgical tool system 10 of this invention. System 10 includes a powered handpiece 12 used to perform a surgical procedure on a patient. The illustrated handpiece 12 is a saw. Internal to the handpiece 12 are a motor 13 and a gear assembly (gear assembly not illustrated). In the illustrated handpiece 12, motor 13 and the gear assembly oscillate a blade 14 removably attached to the distal end of the handpiece 12. ("Distal," it should be understood, means away from the surgeon/towards the patient. "Proximal" it should be understood, means towards the surgeon/away from the patient.) Other handpieces may be provided with other motor or gear assemblies to drive the associated cutting accessories in rotational movement. Blade 14 and other cutting accessories are removably connected to the handpiece 12 and motor 13 by a coupling assembly 15 integral with the handpiece.

The handpiece 12 is removably attached to a control console 16 by a flexible cable 17. The control console 16 supplies the power needed to energize the handpiece motor 13. More particularly, internal to the control console 16 is a handpiece motor driver 18. Handpiece motor driver 18 is capable of supplying the energization signals needed to actuate the handpiece motor 13. These energization signals are supplied to motor 13 through conductors internal to cable 17. A main controller 19 internal to control console 16 generates command signals to the motor driver 18 to ensure that the appropriate energization signals are applied to the handpiece motor 13. In one version of the invention, the GDPXA255A0C300 processor from the Intel Corporation of Santa Clara, Calif. serves as the processor from which main controller 19 is constructed.

The depicted control console 16 has multiple sockets 20. Each socket 20 is capable of receiving a separate cable 17. This allows multiple handpieces 12 to simultaneously be connected to the control console 16. Control console 16 has a display 28 with a touch screen surface. Commands for regulating the components of the system 10 are entered into the control console by depressing buttons presented as images on display 28. Commands are also entered into control console 16 by other control switches. These switches may be integral with the handpieces 12. Alternatively, these switches may be individual switches that are part of a footswitch assembly 30 also attached to the control console. In FIG. 1, footswitch assembly 30 is shown connected to the control console 16 by a cable 32. Control console 16 is provided with two sockets 34 for receiving two cables 32. This allows two footswitch assemblies 30 to be selectively attached to the control console 16.

Figure 3:
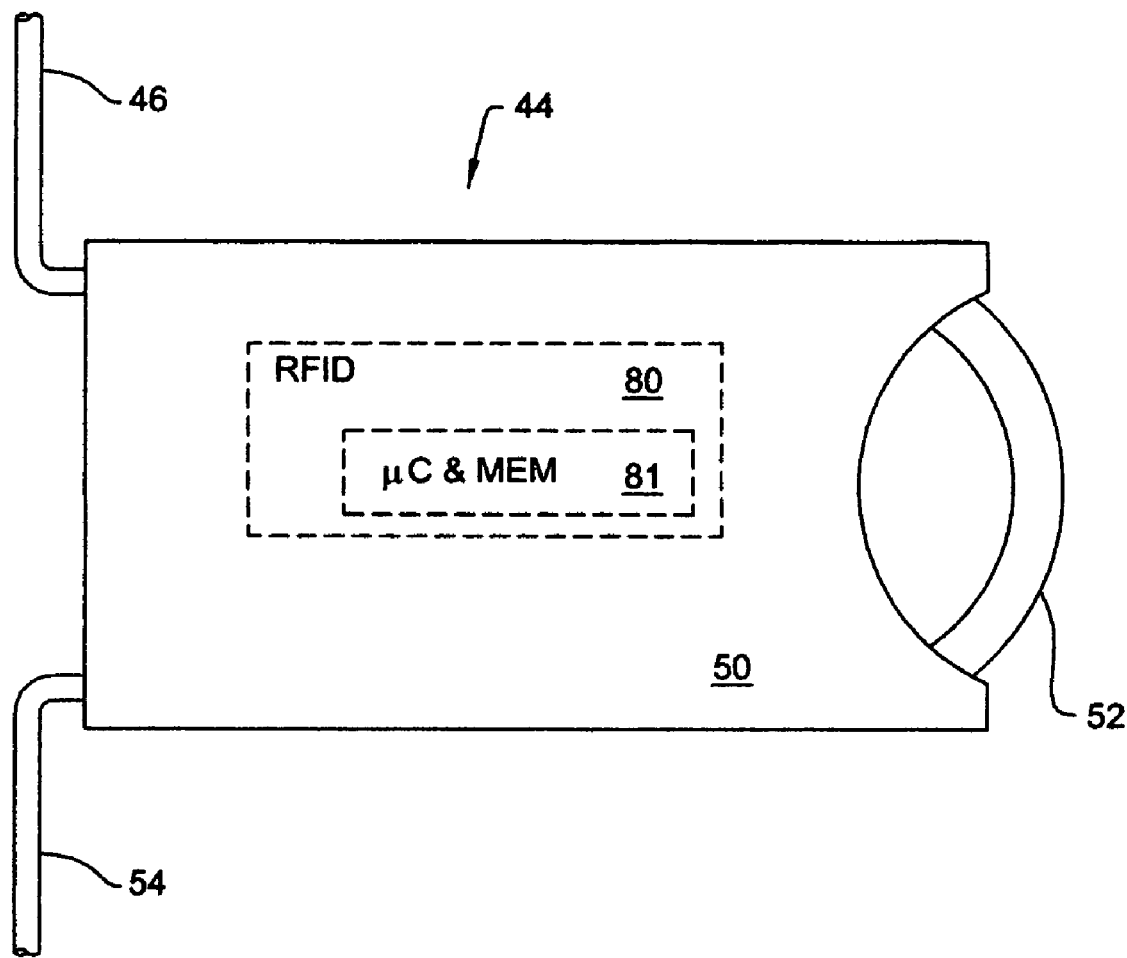
FIG. 3 is a diagrammatic illustration of a tube set cassette of this invention.

System 10 of this invention is also capable of supplying irrigating fluid to the site at which handpiece 12 is used to perform a procedure. The system 10 has a pump 40 that includes both a pump head 42 and a tube set 44. The tube set 44 includes an inlet tube 46. One end of inlet tube 46 is connected to a sterile irrigation fluid source 48, sometimes called a fluid bag. The opposed end of inlet tube 46 extends into a cassette 50, best seen by reference to FIG. 3. This end of the inlet tube 46 is connected a reinforced section of tubing, referred to as pinch tube 52 that extends out of and back into the cassette 50. The opposed section of pinch tube 52 is connected to an outlet tube 54. The outlet tube 54, also part of the tube set 44, extends out of the cassette 50.

The distal end of the outlet tube 54 is connected to an irrigation clip 56 that is removably attached to the outside of handpiece 12. Irrigation clip 56 includes a carrier tube 58 that extends longitudinally along the outside of the handpiece 12. An outlet tube 59 that may be formed from bendable metal tubing, extends forward from the distal end opening of the carrier tube 58 towards the site at which the saw blade 14 is directed. The distal end opening of the irrigation clip outlet tube 59 functions as the port through which the irrigating fluid is discharged.

Pump head 42 is disposed inside the control console 16. The pump head 42 includes a disc shaped neck 62 to which a set of rollers 64 are rotatably mounted. Pump 40 of this invention is assembled for use by inserting the tube set cassette 50 in a slot 66 in the control console so that the pinch tube 52 is pressed between the rollers 64 and an adjacent arcuately shaped outer wall of the cassette. More particularly, at any given instant, at least one roller 64 is pressed against pinch tube 52. The pump head 42 is rotated by a pump motor 68 also disposed inside the control console 16.

After the pump 40 is initially assembled for use, the free end of the inlet tube 46 is attached to the irrigation fluid source 48. Flow of fluid is normally blocked due to the fact one of the rollers 64 presses pinch tube 52 shut against the cassette 50. When irrigation fluid is needed, pump motor 68 is actuated. The actuation of the pump motor 68 results in the rotation of rollers 64 around the center axis of neck 40. The circular motion of the rollers 64 presses the rollers against the pinch tube 52. This action forces the fluid in the pinch tube 52 downstream through the outlet tube 54 and irrigation clip 56 so that it is discharged at the surgical site. Gravity causes replacement fluid to flow through inlet tube 46 into pinch tube 52.

The actuation of the pump motor 68 is controlled by a pump motor controller 69. The pump motor controller 69 receives its instructions regarding when and what rate the pump motor 68 should be actuated from the main controller 19. One possible circuit for assembling motor controller 69 can be constructed out of the ATmega8 microcontroller available from Atmel Corporation of San Jose, Calif., USA.

System 10 of this invention is further constructed so that handpiece 12 is provided with a NOVRAM 70. The NOVRAM 70 contains data that describe the handpiece. These data include data that operating parameters of handpiece motor such as the maximum speed at which the motor can operate and the maximum torque the motor is allowed to develop. The main controller 19 internal to the control console 16 reads the data in the handpiece NOVRAM 70. Based on these data and user-generated commands received by the main controller 19, the main controller causes the motor driver 18 to generate the appropriate energization signals to the handpiece motor 18. The above-mentioned, incorporated-by-reference U.S. Pat. No. 6,017,354 discloses a system for reading data from the handpiece NOVRAM 70 and using these data to regulate the application of energization signals to the handpiece motor 13. This patent also discloses one possible structure for an irrigation clip 56.

Figure 4:
FIG. 4 is a table depicting the data stored in the handpiece NOVRAM in order to facilitate the operation of the system of this invention.

As seen by reference to the table of FIG. 4, handpiece NOVRAM 70 also contains data regarding the characteristics of the irrigation fluid that is to be discharged through companion irrigation clip 56. Specifically, there is a minimum flow rate field 74 in which data are stored that indicates the minimum flow rate through which irrigation fluid can be discharged through clip 56 in order to have any effect. Data in a default flow rate field 76 indicates what is understood to be the preferred flow rate for discharging irrigation fluid through the clip 56. A maximum flow rate field 78 is provided in which data are stored that indicates the maximum rate at which irrigation fluid can be discharged through the clip 56.

It should also be understood that one or more of the fields 74, 76 and 78 may be used to store flag data indicating that the associated handpiece 12 is not one to which an irrigation clip 56 can be attached. These flag data are thus loaded in the NOVRAMs 70 of handpieces that do not support irrigation clips or that do not themselves serve as devices for introducing irrigation fluid to the surgical site. Alternatively, NOVRAM 70 may have a separate single bit flag field that is selectively set depending on whether or not the associated handpiece 12 is configured to possibly receive irrigation fluid.

Internal to the tube set cassette 50 is a radio frequency identification device (RFID) 80. The RFID 80 includes a memory 81 in which data are stored that contain information describing the tube set 44. The RFID also has the following components, none of which are illustrated, that facilitate the reading of data to and the writing of data from memory 81: a coil, a signal modulator/demodulator; a specialized processor; and a rechargeable power supply. One such RFID 80 is the icode-SLI available from Philips Semiconductor.

The types of data stored in the RFID memory 81 are now described by reference to FIGS. 5A and 5B. As discussed below, these data are read by and updated by the main controller 19 to regulate the operation of the pump 40. These data include a family code, stored in a family field 82, that provides basic information regarding the type of device with which the RFID 80 is integral. For example, for this tube set, the family field 82 contains data indicating that the pump is in the powered surgical tools family of medical devices. A device field 83 stores data identifying the specific type of surgical device. Here the data in field 83 indicates the specific type of tube set 44, with which the RFID 80 is integral. The data in fields 82 and 83 are used by the device reading the data to determine whether or not it, or another component, uses the data as decision-making input variables. If the data are used by another component to which the reading device, here control console 16, is connected, the reading device forwards the data to that device.

A length field 84 contains data indicating the length in the RFID memory 81 of following data fields in which data describing the inherent characteristics of the tube set are stored. The data in the length field 84 are used by the main controller 19 to facilitate the further reading of data to and writing data from the RFID memory. Data indicating the format of the remaining data stored in the memory of the RFID 80 are stored in a format revision field 86. The data in field 86 thus indicates the sequence in which the different types of the remaining data in the memory 81 are stored.

Following the format revision field 86, are a part number field 88, a part name field 90, a lot identification field 92, a manufacturer identification field 94, and a data revision field 96. The data in the part number field 88 are a numeric identification of the tube set 44. The data in the part name field 90 is an alphanumeric (ASCII) identification of the tube set 44. The data in the lot identification field 92 identify the manufacturing lot in which the tube set assembled. Lot identification field 92 may also contain a serial number unique to the tube set 44. The data in manufacturer identification field 94 identifies the manufacturer. The data in the manufacturer identification field 94 may also function as key for an authorization algorithm as described hereinafter. The data in the data revision field 96 indicates the version of the data stored in the RFID memory.

The next data fields identify the control console 16 hardware and software with which the tube set 44 can be used. Specifically, there is a minimum console major hardware revision field 100, a major console major software revision field 102 and minimum console software revision field 104. The minimum console major hardware revision field 100 contains data identifying the minimum console major hardware configuration for the control console 16 with which the tube set 44 can be used. The minimum console major software revision field 102 and the minimum console minor software revision field 104 contain data identifying, respectively, the major and minimum software configurations of the software internal to the main controller 19 with which the tube set 44 can be used.

The memory of the RFID 80 also contains data describing the characteristics of the individual tubes of the tube set 44. There are tube in and tube out length data fields 106 and 108, respectively. The data in fields 106 and 108 describe, respectively, the length of the tube set inlet tube 46 and outlet tube 54. Data describing the inner diameters of the inlet and outlet tubes 46 and 54, respectively, are stored in tube in and tube out diameter fields 110, and 112, respectively.

Data identifying the flow rate through the tube set 44 are stored in a flow per revolution field 114. Specifically, the data in field 114 identifies the volume of irrigating fluid that flows through the distal end opening of the outlet tube 54 for each 360° revolution of the pump head 42. The memory of the RFID 80 also contains maximum sustained flow and maximum burst flow fields 116 and 118, respectively. The data in the maximum sustained flow field 116 identifies the maximum sustained flow rate of irrigating fluid through the tube set 44. The data in the maximum burst flow field 118 identifies the maximum burst flow rate of irrigating fluid through the tube set 44.

The RFID 80 also contains pre-stored data related to the usage of the tube set 44. Some of these data are stored in insertion limit and warning fields 122 and 126. Specifically, the data in the insertion limit field 122 indicates the number of times the tube set 44 can be coupled to a control console 19. The data in the insertion warning field 126 indicates the number of times the tube set can be coupled to a control console before a warning is generated. Additional tube set usage data are contained in run time limit and warning fields 124 and 128, respectively. Specifically, the run time limit field 124 contains data indicating the total amount of time the tube set 44 can be used. Data indicating the amount of time the tube set 44 can be used before it is necessary to present a warning are stored in the run time warning field 128.

A single-bit flag indicating whether or not the tube set can be auto-primed is contained in an auto-prime field 130. Fields 132, 134, 136, and 138 are also single bit flag fields. (The majority of the previously and later described fields are all at least one byte in size.) Specifically, field 132 is a tube set disposable field that indicates whether or not the tube set 44 is disposable. Field 134 is a disposable lock field. The flag in field 134 if the control console 16, upon determining that the tube set is a previously used disposable tube set, should inhibit further use of the tube set. Field 136 is a disposable warning field. The flag in field 136 is used to determine whether or not, if it is determined that the tube set 44 is a previously used disposable tube set, a warning should be presented on the control console display 28. Field 138 is a reusable warning field. The flag setting in field 138 is used to determine whether or not, when the tube set 44 is reaching the useful end of its life, a warning should be generated.

In addition to the above-described fields of pre-stored data, the RFID memory 81 contains fields in which data are read from and written into during the operation of the pump 40. An insertions field 140 stores data indicating the number of times the tube set 44 has been coupled to a control console 16. Data indicating the amount of time the tube set 44 has been used to supply irrigating fluid are stored in a run time field 142. An insertion time field 144 stores data indicating when the tube set was coupled to the current control console 16.

Figure 5B:

While not illustrated in FIGS. 5A and 5B, it should be understood that many versions of the invention, the memory of the RFID 80 is also provided with one or more data fields in which cyclic redundancy check data are stored. The data in the cyclic redundancy check fields are error detection or error correction data used by the device reading the data in the RFID 80 to determine whether or the data are correctly read. If the data in the cyclic redundancy check fields are error correction data, these data are also used to correct misread data. In one version of the invention a cyclic redundancy data check field is located after the header data, after the device field 84. A second cyclic redundancy check field is located after the reusable warning flag field 138. Space is also provided in the RFID 80 memory for a third cyclic redundancy field after the insertion time field 144. The control console 16 writes error detection or error correction data into this third cyclic redundancy check field as part of the process of updating the data in fields 140, 142 or 144.

Internal to the control console 16 is an interface 148 for reading data from and writing data to the tube set RFID 80. The interface 148 is connected to the main controller 19 to function as the device through the main processor 19 exchanges data with the tube set RFID 80. Interface 148 includes an antenna that is located immediately adjacent the inner surface of an interior wall of the control console 16 that defines the slot 66 in which cassette 50 is inserted. The antenna is positioned so that when the cassette 50 is positioned in the slot 66, this antenna and the coil integral with the RFID 80 are close enough to facilitate inductive signal transfer therebetween. The interface 148 also includes a modulator/demodulator for encoding the signals for forwarding to the RFID 80 and decoding received signals received from the RFID into a bit stream. In some versions of this invention, signals are exchanged between the tube set RFID 80 and control console interface 148 by selective amplitude shift keying of the carrier signal. In one version of the system of this invention interface 148 is constructed around the SL RC400 I•CODE Reader available from Philips Semiconductors of Eindhoven, The Netherlands.

In constructing system 10 of this invention, care should be taken to ensure that the antenna integral with interface 148 is not positioned so close to the front of control console 16 that it could exchange signals with the REID 80 in a tube set 44 placed in front of the console. Such signal exchange could, as discussed below, result in a false determination that the tube set 44 has been coupled to the control console 16. Thus, collectively, REID 80 must be positioned in cassette 50 and the interface 148 antenna must be located so that only when the cassette is inserted in slot 66 is there inductive signal exchange.

Figure 6A:
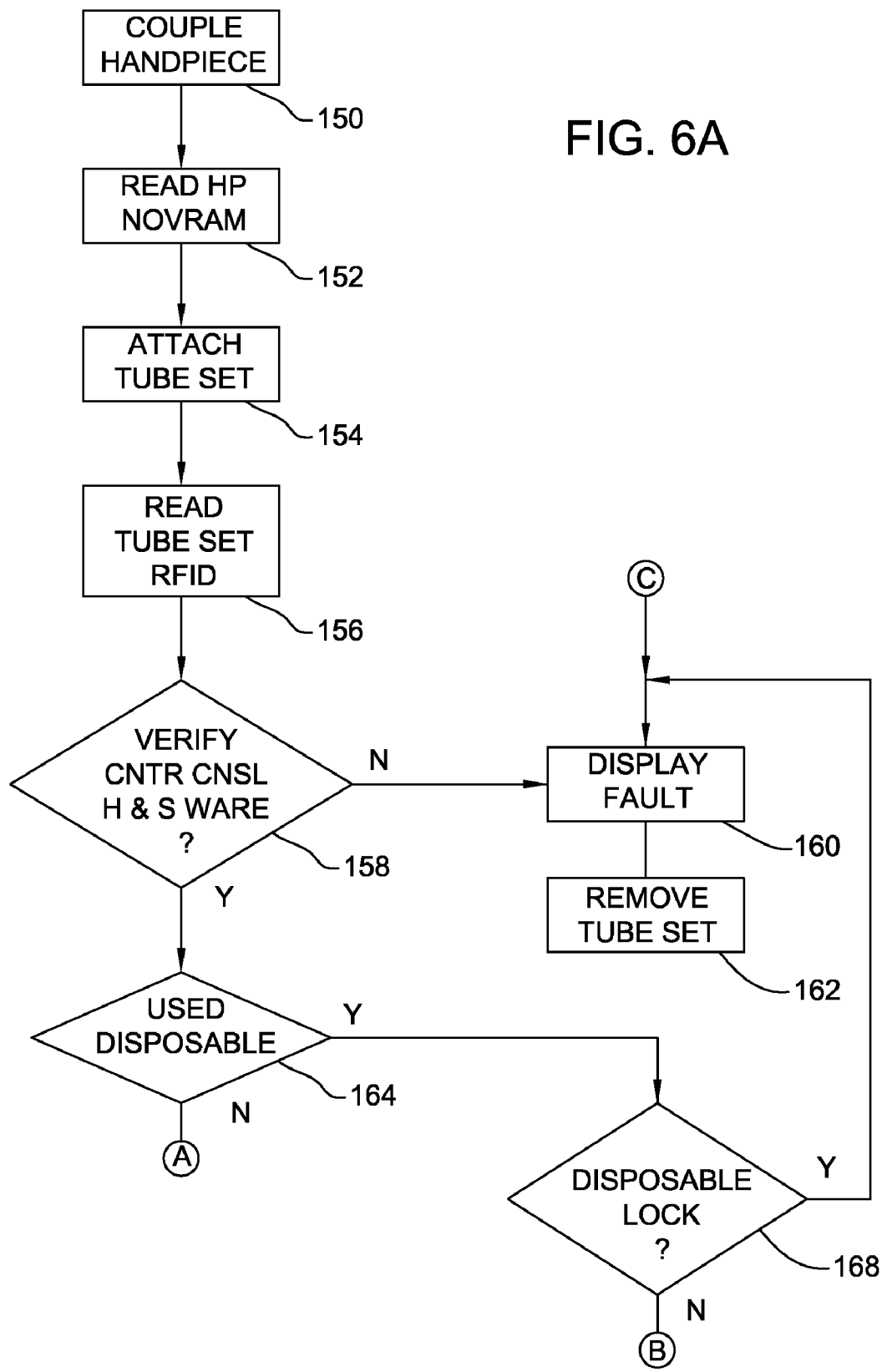
FIGS. 6A, 6B and 6C collectively form a flow chart illustrating how the control console regulates the actuation of the irrigation pump of this invention.
Figure 6B:
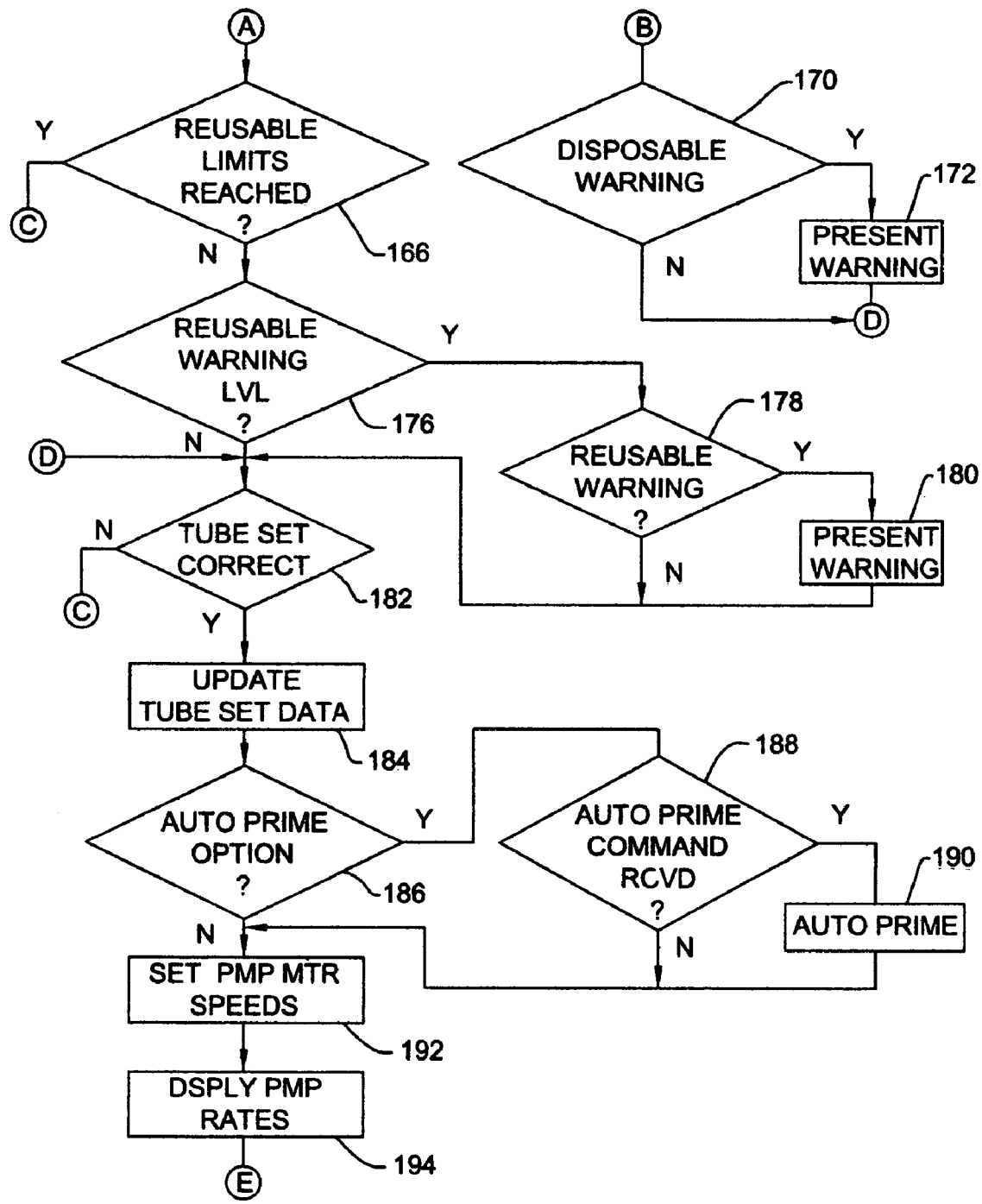
Figure 6C:
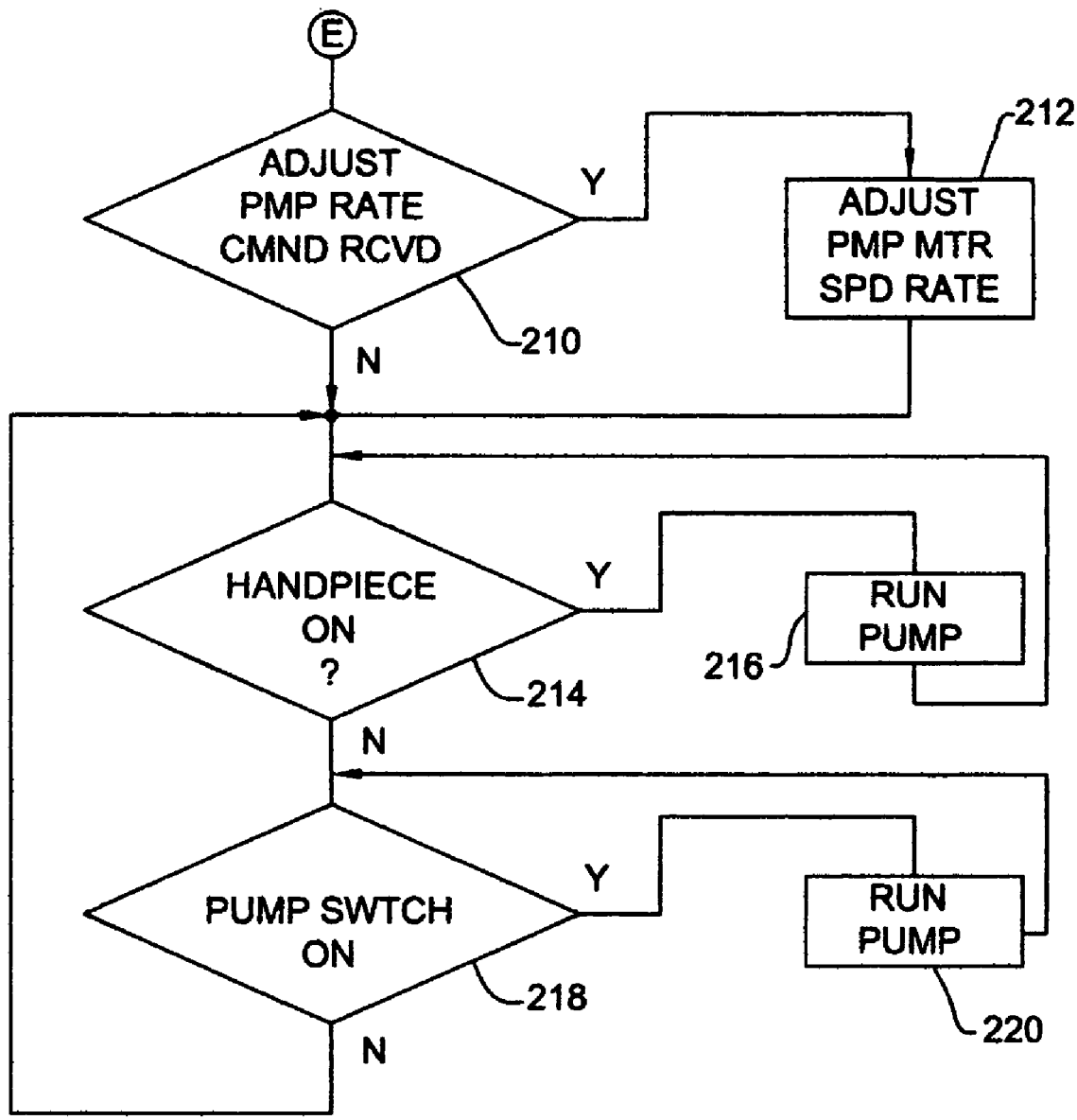

FIGS. 6A, 6B and 6C collectively illustrate how the system 10 of this invention operates. Initially, as represented by step 150, and handpiece 12 is coupled by cable 17 to the control console 16. Upon detecting that the handpiece 12 has been so connected, the main controller 19 reads the data in the handpiece NOVRAM 70 represented by step 152.

Tube set 44 is then attached to the control console 16, as represented by step 154. This attachment is performed by inserting the tube set cassette 50 into the control console slot 66. Also as part of step 154, the distal end of the tube set outlet tube is connected to the inlet fitting on the handpiece irrigation clip 56. Main controller 19 periodically tests to determine whether or not the attachment of step 154 has occurred by broadcasting a read request through interface 148. If no data are returned in response to this request, main controller 19 interprets this response as indicating the tube set 44 is not attached to the control console 16. If data are returned in response to this request, the main controller recognizes the response as indicating a tube set 44 is so attached.

Once the tube set 44 is so attached, the main controller 19 reads the stored data in the RFID memory 81, as represented by step 156. A series of checks are made to determine whether or not the tube set 44 can supply the irrigation fluid needed when the handpiece 12 is actuated. Specifically, in step 158, the control console verifies that it has the hardware and software needed actuate the pump 40 formed in part by the tube set 44. Specifically, based on the data in the minimum console major hardware revision field 100, main controller 19 determines whether or not the control console has the hardware necessary for pumping fluid through the tube set.

Also in step 158, the main controller 19 determines whether it has the minimum major and minor software revisions needed to regulate the flow of fluid through the tube set 44. It is understood that already loaded into the main controller 19 are data identifying the hardware revision of the control console 16 and the major and minor software revisions of the control software executed by the main controller. Based on the data read from the minimum major and minor console software revision fields 102 and 104, respectively, main controller 19 determines whether or not it has the software that is compatible with the tube set 44.

If the control console 16 does not have either the hardware or software necessary to pump and regulate fluid flow through the tube set 44, main controller 19, in step 160, causes a fault message to be presented on the display 28. This message indicates that specific type of fault. Here, the message indicates that the control console 16 does not have minimum hardware or software needed to facilitate fluid flow through the tube set 44. The system 10 then waits for surgical personnel to remove the tube set 44, step 162. A new, more appropriate tube set 44 for the control console 16, is then inserted. (Step 154 is repeated, return link not shown.)

It should be understood that other tests may be performed in step 158 to make an initial determination regarding the appropriateness of the tube set 44. For example, in one supplemental test, the manufacturer's identification data from field 94 may be used to determine whether or not the tube set is manufacturer appropriate allowed for the control console. This test may be performed by testing the manufacturer's identification to determine if it comprises an appropriate authorization code to use the tube set 44 with the control console 16. If the tube set fails this test, in step 160, an appropriate notice of the nature of the tube set fault is displayed.

Another test that may be performed as part of step 158 is whether or not the control console main controller 19 is aware of any potential faults with the specific tube set 44. Specifically, the control console 19 may be connected to a network over which information are broadcast about the components used in the surgical tool system 10. This information can include data indicating that, information has been developed that that tube sets of a particular manufacturing lot should not be used. This information is stored in the memory associated with the main controller 19. Thus, during step 158, the main controller 19 also reviews the lot information from lot identification field 92 from the RFID memory 81. In this review, the lot is checked against the list of restricted tube set lots. If the tube set is from one of the restricted lots, step 160 is executed to cause the generation of an appropriate fault notice on display 28.

Assuming the tube set 44 is one that, from the tests in step 158, it initially appears can be used, step 164 is executed to determine whether or not the tube set is a disposable tube set that was previously used. Initially this test is performed by reviewing the flag in the disposable flag field 132 to determine if the flag setting indicates that the tube set is a disposable (single use) tube set. If the flag setting in field 132 indicates the tube set is reusable, the system executes the below described step 166.

Alternatively, if it is determined that the tube set 44 is disposable, in step 164 a second test is made in this step to determine whether or not the tube set was previously used. One means of performing this test is reading the data in the insertions field 140. The data in field 140 will inform the main processor 19 whether or not the tube set was previously inserted into a control console 16. If the count in field 140 is above zero, the main controller 19 interprets these data as indicating the tube set was previously used. A second means of performing this test is reviewing the data in the run time field 142 to determine whether or not fluid was previously pumped through the tube set 44. If the elapsed time count in field 142 is above zero, the main controller 19 interprets this data as indicating that the tube set 44 was previously used.

Alternatively, the main controller 19 may store a list of serial numbers of the previously attached tube sets 44. The second test of step 164 may consist of reviewing the serial number of the present tube set 44 to determine whether or not it is on that list. If the tube set's serial number is so listed, the main controller 19 recognizes this information as meaning the tube set was previously used.

If, in step 164, it is determined that the current tube set is a previously used disposable tube set 44, main processor 19 determines whether or not the system is prohibited from using this tube set. This step, represented by step 168, consists of reviewing the setting of the flag in the disposable lock field 134. If the flag in field 134 is set to indicate further use of the tube set 44 is prohibited, the main processor executes step 160 and causes an appropriate cause-of-fault message to be displayed.

If, it is determined in step 168 it is not necessary to lock out the further use of the tube set 44, the system proceeds to determine if at least the surgical personnel should receive a warning regarding the previously used-condition of the tube set. In this step, represented by step 170, the state of the flag in disposable warning field 134 is reviewed. If the state of this flag indicates a warning should be generated, in a step 172, main controller 19 causes an appropriate warning to be presented on the display 28. This warning may include an image of a button the surgical personnel need to depress before the system 10 continues to configure itself for operation. The main controller 19 then proceeds to further configure the system 10 for operation, step 182. It should be recognized that, in response to the presentation of the warning in step 172, the surgical personnel may remove the tube set and install a new tube set. (Return to step 154, connection not shown.)

If main controller 19, in step 164 determines that the tube set is not a used disposable tube set, the main controller must then determine whether or not the cassette is a reusable cassette near or at the end of its useable lifespan. This evaluation is initially performed by the test of step 166. Here, main controller 19 determines if either one of the two limits for reusable cassettes has been reached. This determination is first made by comparing the number of times the cassette has been inserted from the data in field 140 to the maximum number of times the cassette can be inserted as set forth by the data in field 122.

Also, in step 166, an evaluation is made to determine whether or not the tube set's use has exceeded that of its useful life span. This test is made by comparing the data in the run time field 142 indicating how long the cassette has been used to the limit for its usage stored in field 124. If the testing indicates that the tube set 44 has been coupled to a control console 16 more than the amount of times specified in the insertions limit field 122 or used more than the time specified in the run time limit field 124, step 160 is generated and an appropriate message is presented on display 28.

If the cassette has not reached the end of its useable life, step 176 is executed. In step 176 a determination is made regarding whether or not the cassette is so near the end of its useful life a warning should be displayed. Step 176 is performed by comparing the number of times the cassette has been inserted, the data from field 140, to the insertion warning level data contained in field 126. Also in step 176, the elapsed run time to which the cassette 50 has been exposed is compared to the run time warning level data from field 128.

If in step 176 it is determined that the cassette 50 has been plugged into a control console 16 enough times to trigger a warning or used enough to trigger a warning, main controller 19 determines if a warning should be presented. This determination, in step 178, is made by determining whether or not the flag in the reusable warning field 138 has been set to indicate that a warning should be generated. If the flag in field 138 indicates a warning should be generated, in step 180, main controller 19 presents the appropriate warning on display 28. Again, based on this warning, the surgical personnel may elect to remove the tube set 44.

Assuming the above tests indicate the tube set is useable, the main controller 19, in step 182 determines whether or not the present tube set 44 can be used to supply the irrigation fluid required by the complementary handpiece 12. Main controller 19 makes this determination based on the data read from handpiece NOVRAM 70 and tube set RFID 80 and the known speed range of the pump motor 68. For example, the data in field 76 of the handpiece NOVRAM 70 indicates the maximum rate at which irrigation fluid may be required when the handpiece is used. The maximum sustained flow rate data in field 116 of the tube set memory 81 indicates the maximum rate at which fluid can continually flow through the tube set. If this flow rate is less than the normal maximum rate for the handpiece 12, than the tube set cannot be used to supply the required flow. A second limit on maximum flow through the tube set is a function of the flow per revolution from field 114 and the known maximum speed of the pump motor 68. Flow rates, it should be recognized are determined by multiplying flow per revolution by motor speed. Flow volumes are determined by multiplying flow rate by time of actuation of the pump motor 68.

The minimum flow rate through the tube set 44 is a function of the controller-known minimum motor speed and the flow per revolution data. This rate, it may be determined in step 182, is greater than one or both of the minimum and default irrigation flow rates for the handpiece. Also, sometimes the irrigation line associated with a handpiece 12 is required to deliver a short burst flow of irrigation fluid. This flow may be a percentage above the maximum flow. Based on the data from the flow per revolution field 114 and in the maximum burst flow field 118, main controller 19, in step 182, may determine that the tube set cannot deliver this burst flow.

If, in step 182, main controller 19 determines that the tube set cannot deliver one or more of the required fluid flows, the main controller 19 executes step 160 to cause an appropriate fault message to be presented on display 28. This gives the operating room personnel the opportunity to remove the tube set, performed step 162, and attach a new tube set, reexcute step 154, that can be used to provide the required irrigation flows.

It should be appreciated that there may be instances when, prior to the attachment of tube set 44, plural handpieces 12 may have been attached to the control console 16. If this is the state of system 10, initially, in step 182, main controller 19 determines to which handpiece 12 the pump 40 is be connected. This determination is initially performed by determining whether or not each of the connected handpieces 12 can potentially receive irrigation fluid.

If only one handpiece can receive irrigation fluid, or only one handpiece is attached to the control console 16, main controller 19, by default assigns pump 40 to that handpiece. If multiple handpieces can receive irrigation fluid, in step 182, main controller 19 initially presents a display instructing the operating room personnel to indicate with which handpiece the pump is to be associated. Based on the received response, the above-discussed evaluation is performed based on the irrigation fluid flow parameters for the designated handpiece.

If, in step 182, it is determined that the tube set 44 can be used to provide the required irrigation flows, the basic insertion data for the tube set are updated in step 184. This step includes rewriting the data in the insertions field 140 to increment by one the number of times the cassette 50 has been inserted in a control console 16. Also, in step 184, the data in the insertion time field 144 are rewritten to indicate when the cassette was inserted into the console 16. The memory associated with the main processor 19 may also store this data for a purpose discussed below.

After the pump 40 is ready for use, the main controller 19 reviews the setting of the flag in the auto-prime field 130 to determine whether or not the tube set 44 is one that can be auto primed, step 186. If the tube set 44 can be auto primed, the main controller 19 causes the display to present an invitation to the surgical staff to prime the pump 40. (Step of presenting the invitation not illustrated.) Step 188 represents whether or not the auto prime command is received.

If, in step 188, the prime command is received, the main processor 19 causes the pump to enter a prime mode, to be primed, represented by step 190. In step 190, the main controller 19 generates commands to the pump motor controller 69. These commands cause the pump motor 68 to be actuated for a select amount of time in order to cause a defined amount of fluid to be forced through the tube set 44. Generally, the volume of the fluid that needs to be forced through the tube set 44 is the volume defined by its tubes. Main controller 19 determines this volume based on the tube length and tube diameter dimensional data for the inlet and outlet tubes 46 and 54, respectively, read from fields 106-112 in the RFID memory 81. The volume within the pinch tube 52 is assumed constant for all tube sets 44 and stored in the main processor 19. The reason the volume of the inlet tube 46 is included as input variable is that when the pinch tube 52 is always held closed by one pump head roller 64. This closure prevents the air from flowing out of the upstream inlet tube 44. Thus, the air in the inlet tube 46 cannot be vented to atmosphere. Consequently, when the inlet tube 46 is first connected to the irrigation fluid source 48, this air blocks downstream flow of fluid into the cassette 50 and pinch tube 52. Therefore one part of the priming process is the purging of air from the inlet tube 46, so that irrigation fluid can flow to the pinch tube 52.

It should be recognized that actual volume of fluid removed during the priming process is less than the total volume of the tubes forming the tube set 44. This is because during the priming process the head of the irrigation fluid flow is not pumped to the immediate distal end of the outlet tube 54. Instead, the priming is performed to bring the head of this fluid flow a distance that is both downstream of cassette 50 and, by extension pump 40, and approximately two to six inches behind the distal end opening of the outlet tube 54. This is done to minimize the likelihood that irrigation fluid that may leak out of the tube set or irrigation clip 56 as a consequence of the priming process.

Main controller 19 determines for how long to run the pump motor 68 in the priming process based on the data in the flow per revolution field 114 indicating the volume of fluid forced out of the tube set 44 for each revolution of the pump head 42. A second variable used to determine how long the pump motor 68 needs to be actuated in order to prime the pump 40 is the speed at which the motor is to be actuated. This speed may, for example be a set low speed operating state for the pump. Alternatively, this speed may be the below-discussed speed pump motor 68 needs to run at so pump 40 will operate at low or default flow rate for the associated handpiece 12.

Once the priming process is complete or if priming is not performed, main controller 19 establishes the speed rates for the pump motor 68, step 192. In step 192, one variable used to set the speed rates for the pump motor is the flow per revolution of the pump head 42 from field 114 in the tube set memory 81. This variable is used as a denominator in a number of separate calculations used to establish the range of motor rates. The numerators for these calculations are the minimum, default and maximum irrigation fluid flow rates for the handpiece 12 from fields 74, 76, and 78 respectively, of the handpiece NOVRAM 70. Thus the minimum speed for the pump motor 68 is determined by dividing the minimum irrigation fluid flow rate by the flow per revolution of the pump head. The preferred and maximum flow rate values are similarly employed as numerators in calculations used to, respectively, determine the pump motor speeds for the default and maximum fluid flow rates.

Figure 7:
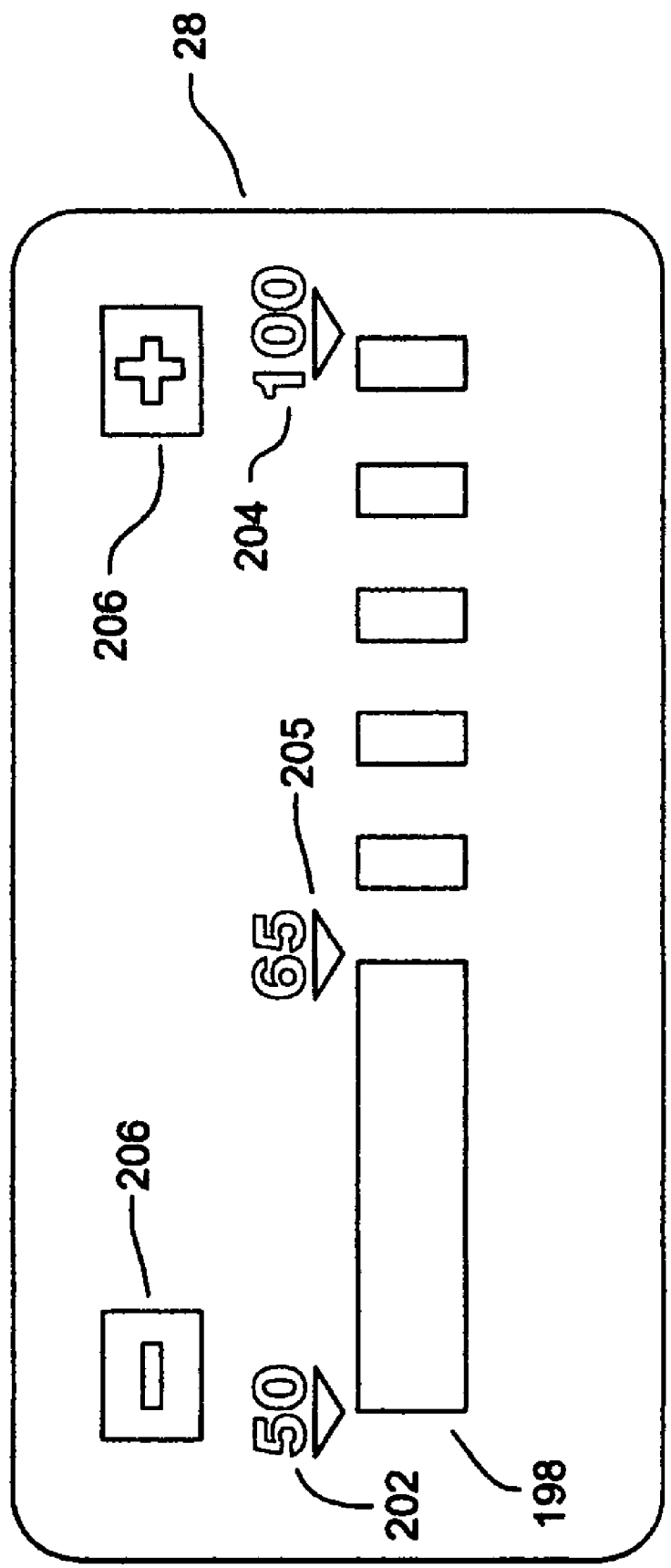
FIG. 7 depicts the information that is presented on the display of the pump regarding the rate at which irrigation fluid is discharged.

Once the pump motor speeds are calculated, the main controller, in step 194 causes an image to be presented on display 28 that informs the surgical personnel of the pump flow rates. As seen by reference to FIG. 7, this image may be in the form of a horizontal bar 198. Above the opposed right end of the bar 198 there is a legend and arrow 202 identifying the minimum fluid flow rate with the selected handpiece 12. Above the opposed left end of the bar there is a legend and arrow 204 identifying maximum fluid flow rate. Between these minimum and maximum values and arrow and legend 205 identify a preferred or default flow rate. This flow rate is based on the default flow rate data from field 76 of the handpiece NOVRAM 70.

It will further be observed that the section of bar 198 to the right of arrow and legend 205 is solid. The section of bar 198 to the left of the arrow and legend 205 are dashed. This is to provide the surgeon with a quick visual indication of how close the pump is to delivering fluid relative to its defined maximum and minimum flow rates.

Also above the opposed ends of bar 198 images of buttons 206 are presented on display 28. These buttons enable manual resetting of the flow rate above or below the default flow rate to a rate preferred by the individual surgeon using the system 10. Initially, as part of step 194, the main controller 192 establishes the speed of the pump motor 68 so that the pump, when actuated for irrigation, will operate at the default flow rate. If the buttons 206 are depressed to adjust the pump rate, step 210, the main controller 19 in step 212, appropriately resets the speed of the pump motor 68. This pump speed is thus independent of the speed at which the pump operates when in the prime mode. The resetting of the fluid flow rate causes arrow and legend 205 to move in the appropriate direction along the bar, the value associated with the legend to change appropriately. The bar likewise fills in or sections with the movement of arrow and legend 205. Again, this is to provide the surgeon with an easily visually discernable indication how close the pump is to operating at its maximum or minimum flow rate.

Assuming the distal end of the outlet tube 54 is connected to an irrigation clip 56, the pump 40 is ready for use.

Main controller 19 monitors the user set switches to determine whether or not the handpiece 12 is to be actuated. Once a command to actuate the handpiece 12 is received, main controller 19 instructs the motor driver 18 to send the appropriate energization signals to the handpiece 12 (not part of this invention). If, in step 214, it is determined the handpiece 12 is to be actuated the main controller, in step 216, causes the pump 40 to be actuated. More specifically, in step 216 main controller 19 instructs the pump motor controller 69 to run the pump motor 69 to run the pump at the appropriate speed to cause irrigation fluid to be discharged at the surgical site at either the default or surgeon-selected flow rate. The pump 40 is continually actuated until, in a reexcution of step 214, it is determined that the handpiece 12 is switched off.

Alternatively, a surgeon, through the depression of a button on display 28, depression of one the foot switches, or a button on the handpiece may, in step 218, actuate the pump 40 independently of the handpiece 12 so as to place the system in an irrigation mode. Once this command is received, the main controller 19 executes a step 220 to actuate the pump 40. The pump remains actuated until, in a reexecution of step 218, it is determined that the surgeon no longer requires irrigation.

Figure 8:
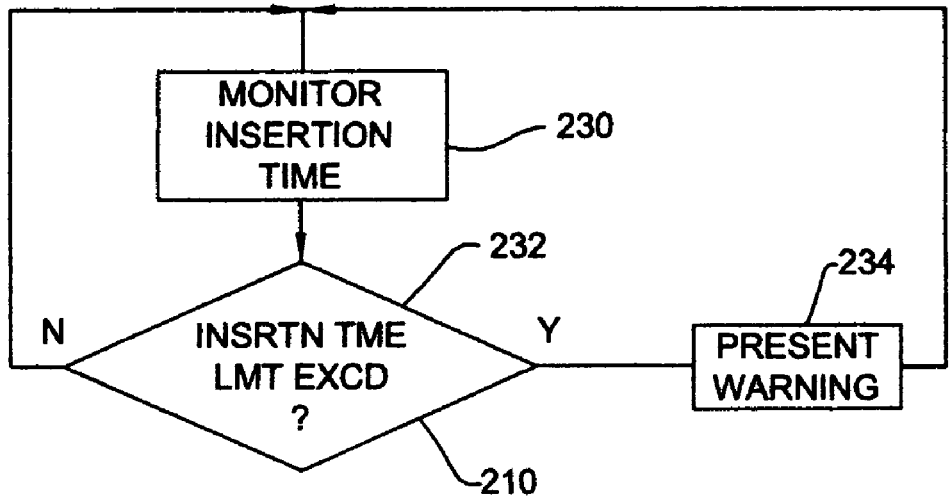
FIG. 8 is a flow chart depicting how the time the tube set is used to regulate the operation of the pump of this system.

As seen by reference to FIG. 8, as long as the tube set 44 remains attached to the control console 16, the time of attachment, referred to as insertion time, is monitored, step 230. This monitoring may be made be reference to the time stamp data in field 144 of RFID memory 81 or a similar time data stored in the memory integral with main controller 19. In a step 232, the main controller determines if this insertion time exceeds a set time limit. This time limit may be programmed into the main controller 19 and may be a value between 2 and 10 hours. If, in step 232, it is determined this time limit has been exceeded, in step 234 main controller 19 causes an appropriate warning to be presented on display 28. This serves to advise the surgical personnel that, given the amount of time the tube set 44 has been out of its packaging there may be a concern regarding its sterility.

Figure 9:
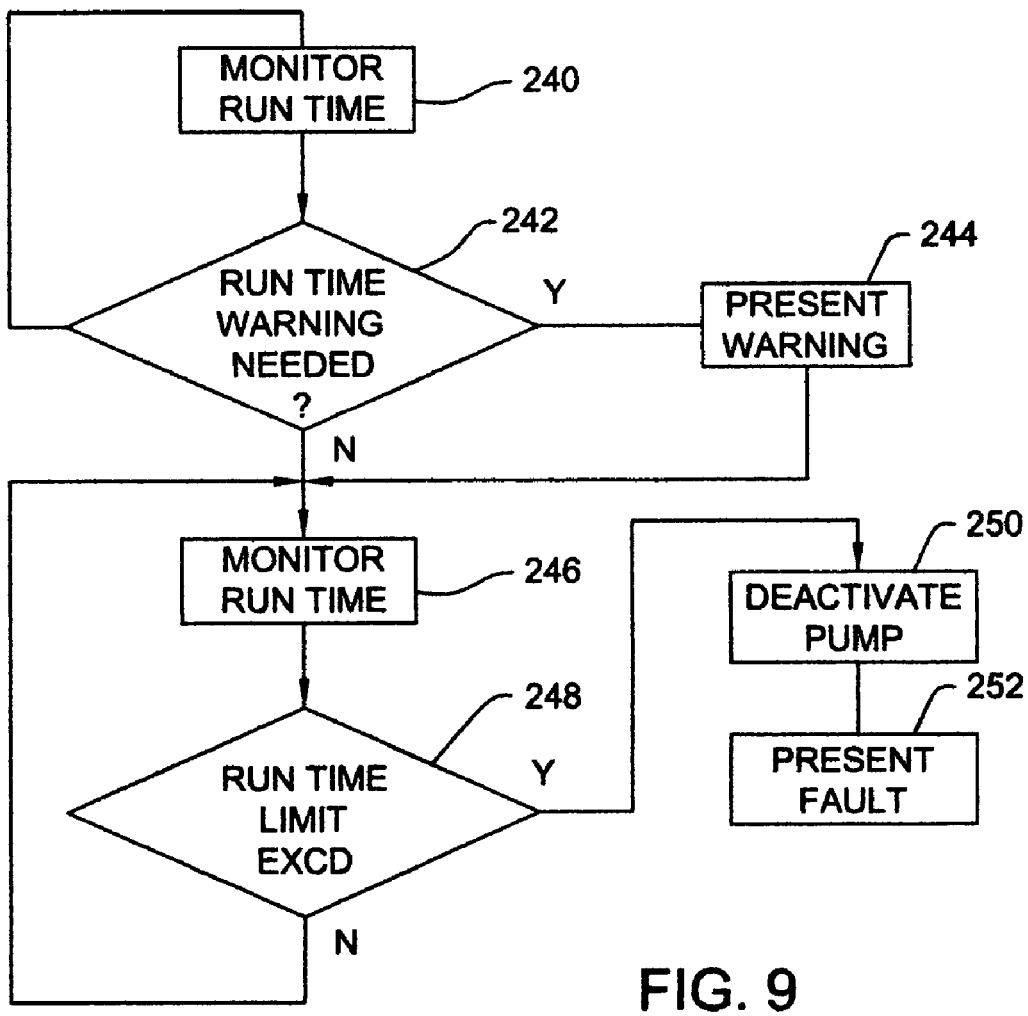
FIG. 9 is a flow chart depicting how the time the pump is operated is used to regulate the operation of pump of this system.

Main controller 19 also monitors the total time the tube set 44 is used as a conduit to actively supply irrigating fluid. This is represented by step 240 of FIG. 9. This monitoring is performed by monitoring the elapsed time the pump motor 68 is actuated. In the event the cassette is reusable, the data from data regarding the prior run time from memory field 142 are summed into the current elapsed time. (Sub-step not shown). In step 244 it can be seen that tests are made to determine whether or not this total run time exceeds the warning run time for the cassette retrieved from memory field 128. If the total run time exceeds the warning run time, main controller 19 causes an appropriate warning message to be presented on display 28, step 244. (In some versions of the invention, steps 240, 242 and 244 are only executed if the flag in field 138 indicates reusable warnings are to be displayed.)

As seen by steps 246 and 248 the run times are also evaluated to determine whether or not the run time for the tube set 44 has exceeded its defined run time. The data for determining the defined run time comes from the memory run time limit field 124. If, in step 248, it is determined this limit is reached, in step 250 the main processor deactivates the pump 40. In step 252, appropriate fault data are presented on display 28.

While not illustrated, it should be understood that, during times when the pump 40 is not actuated, the main controller 19 will periodically have interface 148 retrieve at least some identification data from the tube set RFID 80. These data include data specific to the tube set 44 such as its serial number. Based on whether or not these data change, main controller 19 determines whether or not tube set 44 has been removed and replaced. If such an event has occurred step 156 and the subsequent steps are reexecuted to reconfigure the pump 40 for operation.

In alternative versions of the system 10 of this invention, the main controller 19 may give the surgeon the option of working with a reduced capability pump 40 if the tube set 44 cannot provide the fluid flows normally required by the complementary handpiece 12. In other words the step 182 may be replaced by alternative steps that provide the surgeon with a notice of the reduced capability(ies) of the pump 40 and the option to operate the system 10 with reduced capability pump.

Figure 10:
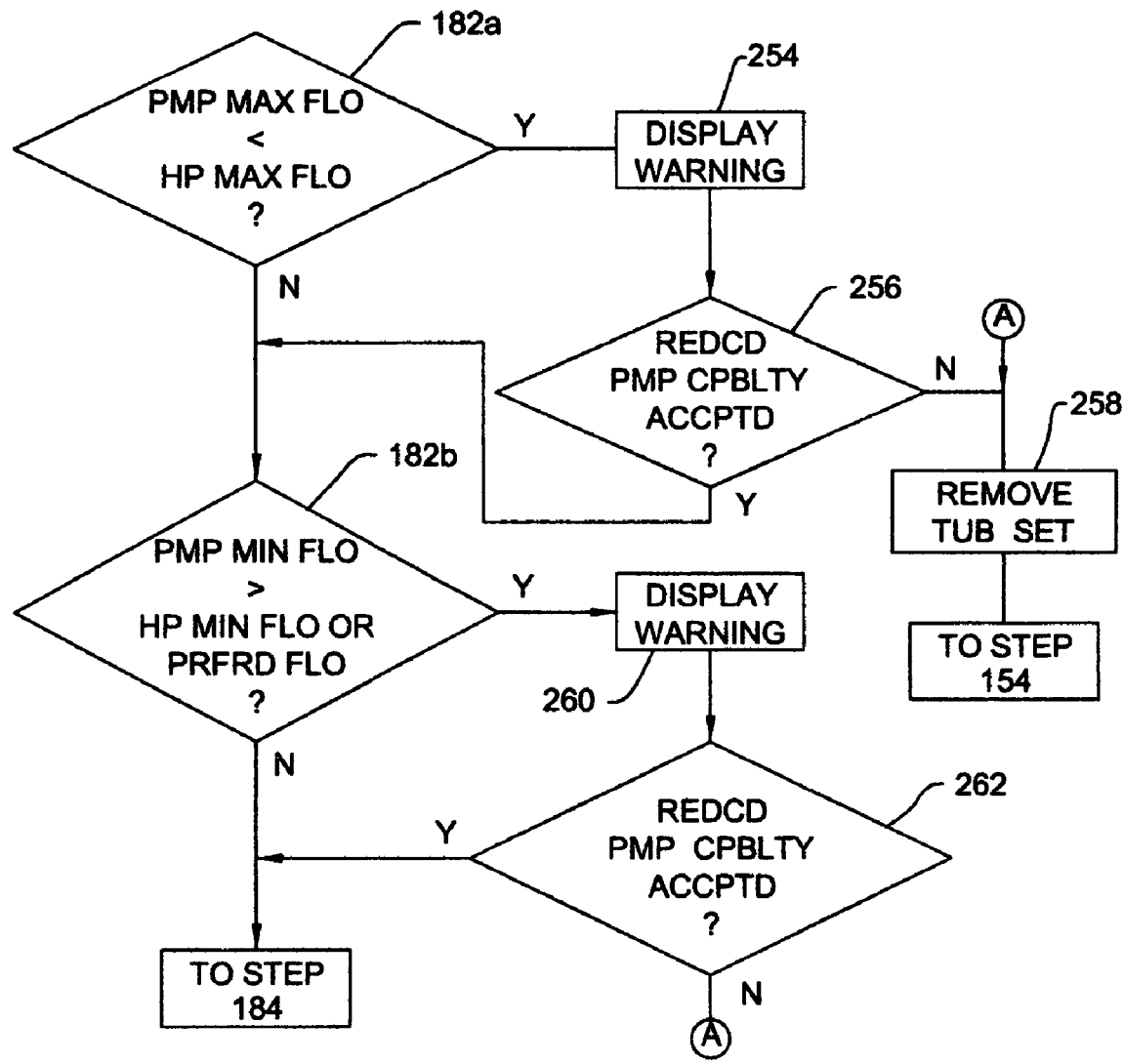
FIG. 10 is a flow chart of how the pump of this invention may configure itself for operating at a reduced capability level.

For example, since the pump motor 68 operates at a known maximum speed, the tube set variables that independently control maximum flow out of the pump are the flow per revolution from memory field 114, the maximum sustained flow rate from field 116 and the maximum burst flow rate from field 118. As discussed above with respect to step 182, the main controller 19 may determine based in part on these data that the pump 40 can not meet either the maximum sustained or burst flow rates for the handpiece 12. However, as represented by FIG. 10, in alternative step 182a, the main controller 19, upon making a determination that one or both of these flow rates cannot be maintained, causes an appropriate warning message to be presented on display 28, step 254. This warning message includes an indication of the particular maximum sustained and/or burst flow rate that can be maintained. The surgeon is given the option of accepting this reduced maximum performance rate, represented by step 256. If the surgeon does not accept this reduced performance, it is necessary to remove the tube set, execute step 258 and install a new tube set capable of meeting the desired performance parameters, reexecute step 154.

A step 182b is then executed if the pump can supply the established high flow rates or the surgeon indicates acceptance of the reduced maximum flow rates. In step 182b a determination is made whether or not the pump can be operated slow enough to provide irrigation fluid at the minimum and default flow rates. If the minimum flow rate through the pump is higher than either of the established minimum or default flow rates, a step 260 is executed to provide the appropriate warning display. In a step 262, the system again receives from the surgeon an indication of whether or not the reduced capability is acceptable. If it is not acceptable, the operating personnel must execute steps 258 and 154 and remove and replace the tube set.

Alternatively, if, in step 262, the surgeon accepts the reduced capability performance of the pump 40, the system proceeds to step 184. The system also proceeds to step 184, if in step 182b, it is determined the pump 40 can supply irrigation fluid at the established minimum and default flow rates. It should then be understood that in the subsequent step 192, the displayed pump flow rates are based on the actual capabilities of the pump 40.

Thus, one version of the system 10 of this invention is configured to ensure that, if a tube set 44 cannot provide the irrigation fluid needed in conjunction with the operation of specific surgical handpiece 12 is fitted to a pump head, use of the assembled pump 40 is blocked. In alternative version of the system 10, the surgeon is given notice of the reduced capabilities of the pump 40 before the pump is allowed to operate. System 10 of this invention thus makes it possible to bring different types of tube sets 44 into an operating room and know that if a potentially incorrect tube set is attached to a pump head 42, the operating personnel will at least have notice of the potential problems.

Still another advantage of the system 10 of this invention is that it allows the tube set manufacturer to assembly tube set from components that collectively provide the tube set for a known useful life. This is because as the tube set 44 reaches the end of its useful life, the system will present a warning to the operating room personnel. Then, when the useful life is reached, inhibit further operation of the pump 40. Thus, a tube set 44 designed to operate for a short period of time can be attached to the system 10 when it is expected the pump 40 will only be used for a short amount of time. A tube set 44 assembled from longer lasting, more expensive components is only used when it is anticipated the pump 40 with which the tube set is integral is to be used for a longer period of time.

Similarly, this system 10 ensures that a reusable tube set 44 or cassette 50 is only used the number of times for which the component is designed to be used.

System 10 of this invention is further designed to, upon insertion of a tube set 44, prime the tube set. This eliminates surgical personnel having to perform this task manually. Alternatively, this priming feature eliminates the initial dry flow out the pump 40 that would otherwise occur when the handpiece is first actuated and the tube set is not primed.

Figure 11:
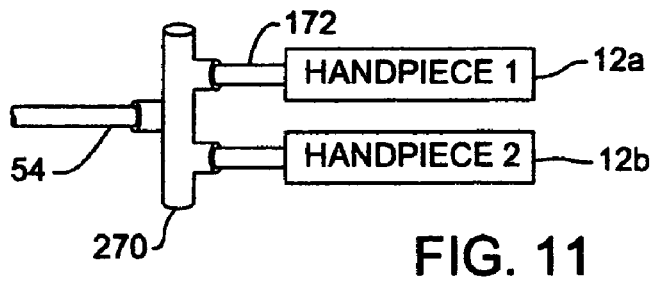
FIG. 11 is a diagrammatic illustration of how the pump of this invention may be used to supply irrigation fluid to plural handpieces.

FIG. 11 illustrates how system 10 of this invention delivers irrigation fluid to two handpieces 12a and 12b. It should be recognized that in this version of the invention it may be necessary to provide the handpieces 12a or 12b or their irrigation clips with valves that regulate fluid flow. Sensors associated with these valves provide an indication of the open/closed state of the valve back to the main processor 19. Only when the sensor signal associated with a valve indicates the valve is open does the main processor consider the handpiece 12a or 12b to be in state in which the surgeon wants irrigation fluid supplied. As seen by FIG. 11, the distal end of the outlet tube 54 is connected to the inlet of a manifold 270. Two outlet lines 272 connected to the outlet end of the manifold 270 deliver the fluid to the individual handpieces 12a and 12b or the irrigation clips, (not illustrated) associated therewith.

Figure 12:
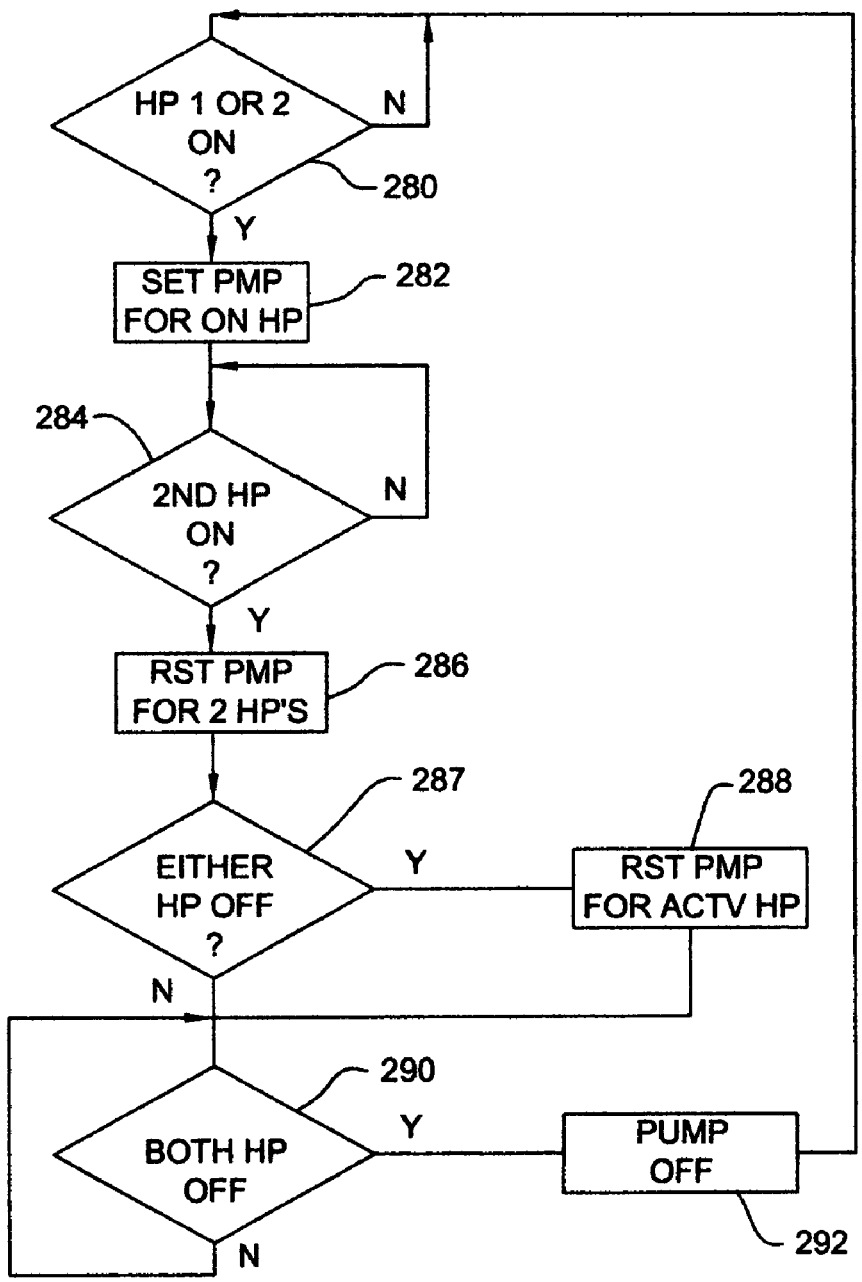
FIG. 12 is a block diagram depicting the process steps employed when the single pump of this invention is used to supply irrigation fluid to plural handpieces.

FIG. 12 depicts the process steps employed by the main controller 19 to regulate the operation of the pump 40 when the pump is configured as illustrated in FIG. 11. Generally, the steps executed in FIG. 12, replace above described steps 214 and 216 of FIG. 6C. In a step 280, main controller 19 monitors the signals received from the handpieces 12a and 12b to determine if either is actuated. If either handpiece 12a or 12b is actuated, in step 282 the pump motor 68 is set to run at the speed needed to deliver fluid at the desired flow rate to the active handpiece. Consequently, irrigation fluid is discharged through the discharge port associated with the active handpiece 12a or 12b.

In step 284, the main controller continues to monitor the non-selected handpiece 12a or 12b to determine whether on not it is actuated. If the second handpiece 12a or 12b is actuated, main controller 19, in step 286, resets the pump motor 68 to a higher speed so that irrigation fluid can be discharged at or near the appropriate flow rates through the discharge ports associated with both handpieces 12a and 12b. It should be understood that, in some configurations, the limited output of the pump 40 may prevent the pump from delivering sufficient irrigation fluid to be able to discharge it at the desired flow rates. However, during the configuration of the system in steps similar to previously described steps 182a, 254 and 256, the surgeons would have been informed of this situation and given the opportunity to not proceed with this particular configuring of the system 10.

In step 287, the main controller 19 determines when either of the two handpieces 12a or 12b is turned off. In response to the deactivation of one of the handpieces 12a or 12b, main controller 19, in step 288, through the pump motor controller 69, resets the pump motor 68 to operate at the speed needed to supply irrigation fluid through the discharge port associated with the still active handpiece 12a or 12b. While not illustrated, it should be understood, the main controller 19 also continues to perform step 284 to monitor whether or not the second handpiece 12a or 12b is reactivated.

As seen by reference to step 290, there will be a time during the operation of the system 10, when main controller 19 determines that both handpieces 12a and 12b are turned off. Once this event occurs, the pump is turned off as represented by step 292. Main controller 19 then continues to monitor whether or not either handpiece is turned back on. Thus, step 280 is reexecuted.

An advantage of the version of the invention depicted by FIGS. 11 and 12 is a single pump 40 supplies the irrigation fluid needed for two handpieces.

Still, it should be understood that in other preferred versions of the invention wherein the system is required, separate pump base units may be provided. Each pump base unit, (not illustrated), includes within a single housing a pump head 42, a pump motor 68 and a pump controller 69 and interface 148. The housing is formed with an appropriate slot for receiving a tube set cassette 50. In these versions of the invention, the pump base unit is networked to the control console 16. More particularly, the pump controller 69 and interface 148 of the pump base unit exchange signals with the control console main processor 19.

In this configuration of the system, when a handpiece 12a or 12b is initially attached to the control console 16, main controller 19 first determines whether or not the handpiece requires irrigation. If the answer is in the affirmative, the main controller 19 assigns the handpiece to either the pump components within the control console 19 or those within the separate pump base unit. Typically, the assignment is done based on which pump head is immediately available, starting with the pump head within the control console 16. The system 10 then operates as previously described. More specifically, after a cassette 50 is inserted into each of the control console and the pump base unit, main controller 19 reads the data from the cassette RFID memories 81. Based on these data and the irrigation flow requirements for the complementary handpiece 12a or 12b, the main controller 19 determines whether or not the associate tube set 44 can deliver the required irrigation fluid.

Thus, in the event the different handpieces 12a and 12b used in single procedure require different irrigation fluid flows, system 10 ensures that the appropriate tube sets 44 are used with each handpiece.

Main controller 19 then monitors the handpieces 12a and 12b for their actuation. When each handpiece 12a or 121b is actuated, the main controller 19 causes the appropriate pump motor 68 to be similarly actuated to cause the desired irrigation flow through the discharge port associated with the active handpiece. If both handpieces 12a and 12b are actuated at the same time, main controller 19 simultaneously actuates both pumps.

Figure 14:
FIG. 14 depicts the data field stored in the memory of the RFID chip associated with the source of irrigation fluid.
Figure 13:
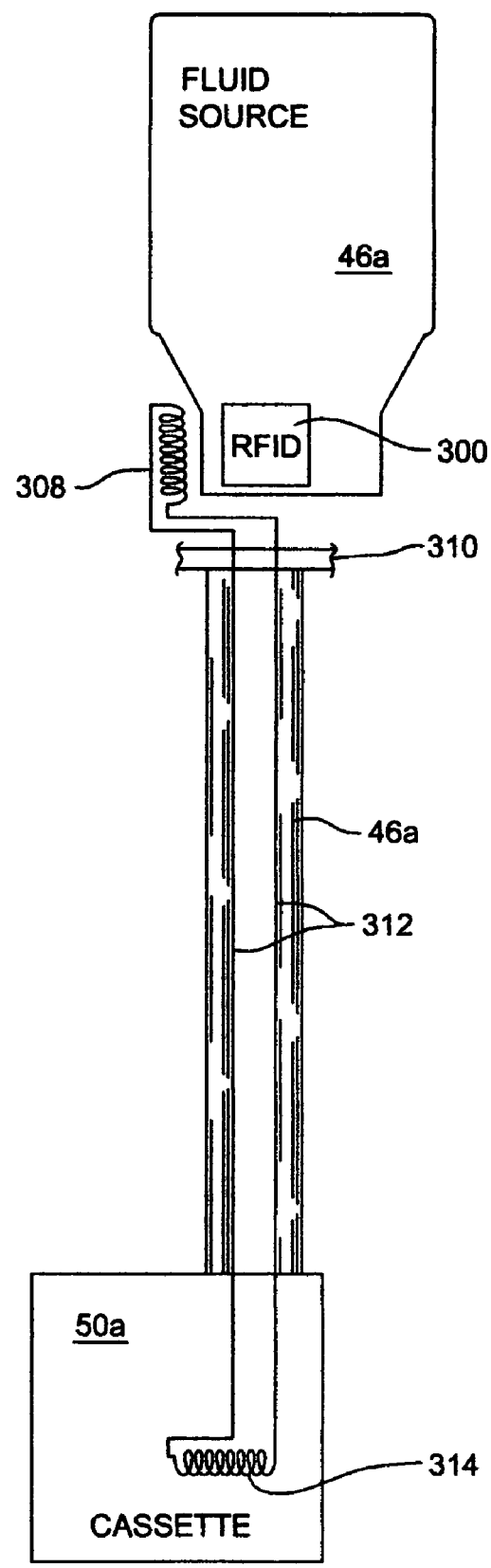
FIG. 13 is a diagrammatic illustration of how the system of this invention may also monitor source of irrigation fluid.

Still other versions of this invention may be used with the fluid source 48a depicted in FIG. 13. Attached to this fluid source is an REID 300 specific to the fluid source. This REID 300 may be covered by a small transparent layer of plastic that extends over the outer surface of the plastic bag forming the fluid source. As represented by FIG. 14, the data internal to the fluid source RFID 300 may contain an indication of fluid type, stored in a fluid type field 302. A fluid volume field 304 contains data indicating the volume of fluid in the source 48a. Data indicating the date the fluid source 48a was manufactured are contained in a date of manufacture field 306.

In order to read the data in the fluid source RFID 300, the tube set is provided with a coil 308. This coil is mounted into an inlet spike 310 attached to the free end of the tube set inlet tube 46a. Conductors 312 that extend longitudinally along the outside of the inlet tube 46a connect coil 308 to a second coil 314 disposed inside the cassette 50a. While not illustrated, it should be understood that the control console is provided with a second interface 148. When the cassette 50a is fitted to the control console, this second interface 148 is configured to exchange signals with coil 314 so that there is an inductive signal connection between coil 308 and the source RFID 300.

Versions of the system 10 of the invention capable of reading data from the fluid source 46a, further configure the operation of the pump based on these data. For example, sometimes the surgeon is capable of inputting into the system data identifying the type of surgery to be performed. Either the main controller 19 or another processor to which the control console 16 is networked maintains a list of the type of irrigation fluids that can or should be used for particular procedures. Based on the fluid type data read from the fluid source RFID 300 field 302, main controller 19 determines whether or not the type of fluid in bag 46a is appropriate. If the fluid type is inappropriate, main controller 19 will cause an appropriate warning message to be presented on the display 28 and/or inhibit actuation of the pump.

Similarly, main controller 19, based on the data indicating the volume of fluid in the source bag 46a, determines whether or not there is sufficient fluid for the procedure. Other variables into this determination are the flow rate data from the handpiece NOVRAM 70 and, possibly, the data the surgeon enters identifying the type of procedure to be performed. These latter data, from the handpiece 12 and the surgeon, are used by the main controller 19 to estimate the amount of fluid needed in order to perform the procedure. The data in the RFID fluid volume field 304 may indicate there is insufficient to perform the procedure. Main controller 19 may then review if source bags 46a containing larger amounts of fluid are available. If such source bags are available, main controller 19 presents a warning notice to the surgeon on the display 28 suggesting a larger bag be provided. This version of the system 10 reduces the likelihood it will be necessary to interrupt the surgical procedure in order to have to change and replace an empty fluid source bag 46a.

The data of manufacture data from RFID field 306 is also reviewed the main controller 19. Specifically, based on these data and the current date, the main controller 19 determines whether or not the fluid in the bag may be so dated that its sterility or chemical efficiency has degraded to the level at which the fluid should not be used. If the main controller 19 makes this determination, a warning is presented on the display 28 and/or use of the pump 40 is inhibited until a new source bag 46a is provided.

Main controller 19 also uses the data from source bag 46a during the operation of the pump 40. Specifically, based on the data from the volume field 304, the data from the flow per revolution field 114 and the amount of time and speeds at which the pump motor 68 is run, main controller 19 determines the amount of fluid remaining in the source bag 46a. Upon the fluid reaching a specific level, the main controller 19 causes an appropriate warning to be presented to the surgeon. This provides operating room personnel the opportunity to replace the nearly empty source bag 46a with a full bag before the surgery enters a point in which it is not be desirable to interrupt the procedure in order to make this replacement.

Alternatively, upon the main controller 19 determining the amount of fluid in the source bag 46a has reached a defined low level, the main controller invites the surgeon to operate the pump in a fluid conservation mode. Specifically, upon the determination that there is a set low volume of fluid in bag 46a, main controller 19 generates a warning informing the surgeon of this fact. Integral with this warning is an invitation to run the pump 40 at a slightly lower speed to reduce the rate of fluid discharge. Thus if the surgeon is nearing the end of the procedure and does not anticipate needed a large volume of irrigation fluid, he/she can conserve the remaining fluid. This avoids the added expense and time interruption associated with having to replace an empty bag when all that is required is conservative management of the remaining fluid.

It should be recognized that the above method of pumping of this invention may be practiced without requiring a fluid source bag with an RFID chip. Specifically, during the initial configuration of the system, for example after step 184, the main controller 19 can direct the operating room personnel to enter through display an indication of the volume of the fluid in the source bag 46. These data are used by the system 10 to enable the conservation of fluid as described above.

The above description is directed to certain preferred versions of the invention. It should be recognized that other versions of the invention may have features and alternative components that are different from what has been described. For example, the described system 10 is designed to actuate motorized powered surgical handpieces. Other versions of the invention may include a control console designed to actuate a handpiece with a power generating unit that emits another form of energy such as light energy, RF energy or ultrasonic energy Similarly, it should be appreciated that not all handpieces with which the system of this invention is employed may contain a detachable irrigation clip. In some versions of the invention, an irrigation flow line may be built into the handpiece. In these versions of the invention, it is anticipated that an individual handpiece will have a fitting such as leur fitting. The distal end of the outlet tube 54 is attached to this fitting as part of the process for configuring the system 10.

Moreover, some handpieces of the system 10 of this invention may be irrigation only handpieces. Still other handpieces may be designed to provide irrigation and suction either simultaneously or sequentially. These particular handpieces do not have powered components. The pump 40 of the system 10 of this invention may still be connected to these handpieces. When the pump 40 is to be used with one of these handpieces, main controller 19, in lieu of step 182, presents on the display 28 a message. The message informs the surgeon that, based on the characteristics for the pump motor 68 and of the tube set 44 as read from the RFID 80, the pump 40 can be connected to a irrigation tool and deliver flows between a given range. The surgeon is then invited to establish a selected flow rate for when irrigation is needed. Once the system 10 is configured, the main controller 19 performs step 218 to monitor if the surgeon has entered a command to actuate the pump. If such a command is entered, step 220 is executed so as to actuate the pump 40.

The above description of the preferred embodiments of this invention should also make it clear that there is no requirement that all fixed equipment of the system of this invention, the pump head 42, the pump motor 68, the pump driver 69 and interface 148 be in a console that also regulates the energization of the handpiece to which the pump is coupled. Sometimes these components may be in separate pump base unit. This base unit may be connected to the handpiece control console over a network, for example over a 1394 interface. In these versions of the invention, the base unit will forward to a control processor the data read from the tube set RFID 80 describing the characteristics of the tube set 44. Based on these data as well as the irrigation fluid requirements of the handpiece 12, this separate control processor determines whether or not the assembled pump 40 can deliver irrigation fluid at requisite flow rates. Similarly, whenever the separate control processor determines the handpiece is to be actuated or the surgeon requires independent irrigation, the control processor sends a command via the network to the pump base unit to actuate the pump motor 68.

It should likewise be understood that pumps of this invention may have different structures than what has been described. For example, in some versions of the invention, internal to the cassette there may be pump chamber with an impeller. This impeller may have fixed vanes or a head with moving vanes that create a suction force. The complementary fixed pump motor includes some type of shaft that couples to the impeller. In these versions of the invention, the data from the tube set RFID memory 81 indicates the flow volume per revolution of the moving component in the cassette. Based on these data, the downline processing components are able to set the speeds for the pump motor so that irrigation fluid is delivered at the desired flow rates. Also, some pump assemblies, to avoid the costs associated with providing a cassette, having a set of linearly aligned plungers. These plungers, which form the pump head, selectively compress and release a section of the tube so that for each cycle, a defined volume of fluid is forced through the tube set.

Likewise, there is no requirement that in all versions of the invention, the data describing the characteristics of the tube set be stored in an RFID. In other versions of the invention, these data may be stored in a ROM integral with the tube set. This ROM is electrically connected to the associated processor that reads the stored data by contacts in the control console or pump base unit.

Likewise, there may be variations in the data stored in the memory associated with the tube set. For example, in some versions of the invention, instead of storing data indicating the flow per revolution or cycle of the pump pumping component, data may be stored indicating the flow out of the tube set pump chamber per revolution or cycle. For the illustrated tube set, it is understood the pump chamber is the space within the pinch tube 52. If the pump cassette has an impeller, the flow data could describe the pump chamber is the space in which the impeller is seated. For a sequential plunger pumps, the pump chamber is the space within the tube section that is cyclically compressed by the plungers.

In some versions of the invention, it may not be necessary to provide the tube set memory with all the data described by reference to FIGS. 5A and 5B. Similarly, in some versions of the invention, it may not be necessary to provide the tube set with a cassette. In these versions of the invention, the RFID or other memory element may be mounted to one of the actual tubes forming the tube set. For example with a pump that includes plungers as a pump head, the RFID can be mounted to small plastic ring. When the tube set is fitted to the fixed components of the pump, the ring is fitted to be adjacent the plungers and a complementary interface.

Similarly, it should be understood that the process steps executed by the control console to configure the pump 40 for operation and control the actuation of the pump may vary from what has been described. For example, immediately upon the tube set 44 being inserted into the control console step 184, wherein the usage field data in the RFID memory 81 are updated, may be executed. This ensures that a use-once tube set would be considered used, even it was simply just only attached to the control console 19. This may be desirable to ensure only completely sterile tube sets are employed. Similarly, the steps of determining whether or not the tube set 44 is a previously used, single use tube set or a reusable tube set that has been used beyond its limits may be performed earlier in the process. Likewise, the steps of setting pump speed, display flow rates and adjusting flow rate, steps 192, 194, and 212, respectively, may similarly performed earlier in the process than described.

Likewise, the steps in which the main controller 19 actually blocks out use of a tube set 44 for one or more reasons may be eliminated. Instead, the main controller 19 may only present a warning regarding the fault condition. This would allow the surgical personnel to decide that for reasons such as efficiency or in an emergency condition, to use a particular tube set.

Therefore, it is an object of the appended claims to cover all such modifications and variations that come within the true spirit and scope of this invention.

What is claimed is:

1. A method of operating a surgical irrigation pump, said method including the steps of:
   attaching a tube to a variable speed irrigation pump, the tube having a proximal end connected to a fluid source and a distal end connected to an irrigation discharge device having an outlet port through which fluid is discharged to a surgical site;
   reading data in a memory attached to the tube, the data including: data for regulating the speed of the pump in a prime mode; and data for regulating the speed of the pump in an irrigation mode;
   accepting a user-entered command that adjusts the speed of the pump when in the irrigation mode;
   in response to a user-entered prime command, operating the pump in prime mode in which the pump is actuated based on the data for regulating the operation of the pump in the prime mode so that the pump operates at a speed that is not based on the user-entered command adjusting the speed of the pump in the irrigation mode wherein, the pump is operated for a select amount time so that a fluid head is pumped to a location downstream of the pump and proximal to the irrigation discharge device outlet port; and
   in response to a user-entered run command, operating the pump in an irrigation mode in which the pump is actuated based on the data for regulating operation of the pump in the irrigation mode and at a speed based on the user-entered command adjusting the speed of the pump so as to cause the discharge of fluid from the tube and the irrigation discharge device outlet port to the surgical site wherein the pump is continually actuated as long as the user-entered run command is entered and, when entry of the user-entered run command is terminated, the pump is deactivated.

2. The method of operating a surgical irrigation pump of claim 1, wherein, in said step of operating the pump to run in the prime mode, the pump is actuated for a select amount of time to cause the fluid head to be pumped to a position proximal to the distal end of the tube.

3. The method of operating a surgical irrigation pump of claim 1, wherein:
   in said step of reading data from the memory attached to the tube, data describing at least one of the tube length or tube diameter are read from the memory; and
   in said step of actuating the pump to run in the prime mode, the read data describing at least one of the tube length or tube diameter are used to regulate the amount of time the pump is actuated.

4. The method of operating a surgical irrigation pump of claim 1, wherein:
   in said step of attaching the tube to the pump, the attached tube is part of a tube set that includes a cassette to which said tube is attached, the memory containing the data for regulating operation of the pump is attached to the cassette and the cassette is attached to the pump; and
   in said step of reading data in the memory attached to the tube, the data are read from the memory attached to the cassette.

5. The method of operating a surgical irrigation pump of claim 1, wherein, in said operation of the pump, the pump is actuated by pressing a portion of the pump against the tube to force fluid through the tube.

6. The method of operating a surgical irrigation pump of claim 1, wherein the data read from the memory attached to the tube for regulating the operation of the pump in a prime mode are different from the data read from the memory for regulating the operation of the pump in an irrigation mode.

7. A method of operating a surgical irrigation pump, said method including the steps of:
   attaching a tube to an irrigation pump, the tube having a proximal end connected to a fluid source and a distal end connected to an irrigation discharge device having an outlet port through which fluid is discharged to a surgical site;
   reading data in a memory attached to the tube, the data including: data for regulating the operation of the pump in a prime mode; and data for regulating the operation of the pump in an irrigation mode;
   accepting user-entered commands to adjust the operation of the pump when in the irrigation mode;
   in response to a user-entered prime command, operating the pump in a prime mode in which the pump is actuated for a select amount time based on the data for regulating operation of the pump in the prime mode so that a fluid head is pumped to a location downstream of the pump and proximal to the irrigation discharge device outlet port wherein, operation of the pump in the prime mode is not based on any user-entered commands for adjusting the irrigation mode operation of the pump; and
   in response to a user-entered run command, operating the pump in an irrigation mode based on the data for regulating operation of the pump in the irrigation mode and any user-entered adjustments to the irrigation mode operation of the pump so as to cause the discharge of fluid from the tube and the irrigation discharge device outlet port to the surgical site, wherein the pump is actuated as long as the user-entered run command is received and, when entry of the user-entered run command is terminated, the pump is deactivated.

8. The method of operating a surgical irrigation pump of claim 7, wherein in said step of actuating the pump to run in the prime mode, the pump is actuated for a select amount of time to cause the fluid head to be pumped to a position proximal to the distal end of the tube.

9. The method of operating a surgical irrigation pump of claim 7, wherein:
   in said step of reading data from the memory attached to the tube, data describing at least one of the tube length or tube diameter are read from the memory; and in said step of actuating the pump to run in the prime mode, the read data describing at least one of the tube length or tube diameter are used to regulate the amount of time the pump is actuated.

10. The method of operating a surgical irrigation pump of claim 7, wherein:
   in said step of attaching the tube to the pump, the attached tube is part of a tube set that includes a cassette to which said tube is attached, the memory containing the data for regulating operation of the pump is attached to the cassette and the cassette is attached to the pump; and
   in said step of reading data in the memory attached to the tube, the data are read from the memory attached to the cassette.

11. The method of operating a surgical irrigation pump of claim 7, wherein, in either of said steps of actuating the pump, the pump is actuated by pressing a portion of the pump against the tube to force fluid through the tube.

12. The method operating a surgical irrigation pump of claim 7, wherein, in said step of reading data from the memory attached to the tube, the data in the memory are read by a wireless exchange of signals.

13. The method of operating a surgical irrigation pump of claim 7, wherein the data read from the memory attached to the tube for regulating the operation of the pump in a prime mode are different from the data read from the memory for regulating the operation of the pump in an irrigation mode.

14. The method of operating a surgical irrigation pump of claim 7, wherein:
   in said step of attaching the tube to an irrigation pump, the tube is attached to a variable speed pump;
   in said step of operating the pump in the irrigation mode, based on user-entered adjustments to the irrigation mode operation of the pump, the speed of the pump is adjusted.

15. A method of operating a surgical irrigation pump, said method including the steps of:
   attaching a tube to a variable speed irrigation pump, the tube having a proximal end connected to a fluid source and a distal end connected to an irrigation discharge device having an outlet port through which fluid is discharged to a surgical site;
   reading data in a memory attached to the tube, the data including: data for regulating the operation of the pump in a prime mode; and data for regulating the operation of the pump in an irrigation mode;
   accepting user-entered commands to adjust the operation of the pump when in the irrigation mode;
   displaying data indicating the operating rate of the pump in the irrigation mode, the operating rate being a function of the speed of the pump;
   in response to a user-entered prime command, operating the pump in a prime mode in which the pump is actuated for a select amount time based on the data for regulating operation of the pump in the prime mode and at a speed independent of any user-entered commands adjusting the operation of the pump when in the irrigation mode so that a fluid head is pumped to a location downstream of the pump and proximal to the irrigation discharge device outlet port, wherein, operation of the pump in the prime mode is not related to the displayed data indicating the operating rate of the pump in the irrigation mode; and
   in response to a user-entered run command, operating the pump in an irrigation mode by actuating the pump based on the data for regulating operation of the pump in the irrigation mode and at speed based on any user-entered commands adjusting the operation of the pump when in the irrigation mode so that the pump operates at a the displayed operating rate so as to cause the discharge of fluid from the tube and irrigation discharge device outlet port to the surgical site wherein, when the pump is operated in the irrigation mode, the pump is actuated as long as the user-entered run command is entered and, when entry of the user-entered run command is terminated, the pump is deactivated.

16. The method of operating a surgical irrigation pump of claim 15, wherein:
   in said step of reading data from the memory attached to the tube, data describing at least one of the tube length or tube diameter are read from the memory; and
   in said step of actuating the pump to run in the prime mode, the read data describing at least one of the tube length or tube diameter are used to regulate the amount of time the pump is actuated.

17. The method of operating a surgical irrigation pump of claim 15, wherein, in either of said steps of actuating the pump, the pump is actuated by pressing a portion of the pump against the tube to force fluid through the tube.

18. The method operating a surgical irrigation pump of claim 15, wherein, in said step of reading data from the memory attached to the tube, the data in the memory are read by a wireless exchange of signals.

19. The method of operating a surgical irrigation pump of claim 15, wherein the data read from the memory attached to the tube for regulating the operation of the pump in the prime mode are different from the data read from the memory for regulating the operation of the pump in the irrigation mode.

20. The method of operating a surgical irrigation pump of claim 15, wherein in said step of actuating the pump to run in the prime mode, the pump is actuated for a select amount of time to cause the fluid head to be pumped to a position proximal to the distal end of the tube.

* * * * *